United States Patent [19]
Werner et al.

[11] Patent Number: 5,877,162
[45] Date of Patent: Mar. 2, 1999

[54] SHORT EXTERNAL GUIDE SEQUENCES

[75] Inventors: Martina Werner; Shaji T. George, both of New York, N.Y.

[73] Assignee: Innovir Laboratories, Inc., New York, N.Y.

[21] Appl. No.: 615,961

[22] Filed: Mar. 14, 1996

[51] Int. Cl.[6] .......................... C07H 21/02; C12D 19/34; A61K 31/00

[52] U.S. Cl. .......................... 514/44; 536/23.1; 536/24.5; 435/6; 435/91.31; 435/91.33; 435/172.1; 435/320.1; 435/325; 435/370

[58] Field of Search .................................. 536/23.2, 23.1, 536/24.5; 435/6, 91.31, 91.33, 172.1, 240.1, 240.2, 370, 320.1, 325; 514/44

[56] References Cited

U.S. PATENT DOCUMENTS

| | | | |
|---|---|---|---|
| 4,104,466 | 8/1978 | Tsuchida et al. | 542/433 |
| 4,868,116 | 9/1989 | Morgan et al. | 435/240.2 |
| 4,980,286 | 12/1990 | Morgan et al. | 435/172.3 |
| 4,981,957 | 1/1991 | Lebleu et al. | 536/27 |
| 4,987,071 | 1/1991 | Cech et al. | 435/91.31 |
| 5,166,320 | 11/1992 | Wu et al. | 530/395 |
| 5,168,053 | 12/1992 | Altman et al. | 435/91 |
| 5,225,337 | 7/1993 | Robertson et al. | 435/91 |

FOREIGN PATENT DOCUMENTS

| | | |
|---|---|---|
| 321021 A2 | 6/1989 | European Pat. Off. |
| 321021 A3 | 6/1989 | European Pat. Off. |
| 2 146 525 | 4/1985 | United Kingdom |
| WO 88/04300 | 6/1988 | WIPO |
| WO 89/05852 | 6/1989 | WIPO |
| WO 89/07136 | 8/1989 | WIPO |
| WO 90/02806 | 3/1990 | WIPO |
| WO 91/04319 | 4/1991 | WIPO |
| WO 91/04324 | 4/1991 | WIPO |
| WO 92/03566 | 3/1992 | WIPO |
| WO 93/01286 | 1/1993 | WIPO |
| WO 93/22434 | 11/1993 | WIPO |
| WO 94/13791 | 6/1994 | WIPO |
| WO 94/13833 | 6/1994 | WIPO |
| WO 95/23225 | 8/1995 | WIPO |
| WO 95/24489 | 9/1995 | WIPO |
| WO 95/27480 | 10/1995 | WIPO |
| WO 9618733 A | 6/1996 | WIPO |

OTHER PUBLICATIONS

Usman et al., Chemical modifications of hammerhead ribozymes: activity and nuclease resistance. *Nucleic Acids Symposium Series* No. 31:163–164, Nov. 9, 1994.

Krupp "Antisense Oligoribonucleotides and Rnase P. A Great Potential" *Biochimie* vol. 75:135—139, 1993.

Yuan et al "Selection of Guide Sequences That Direct Efficient Cleavage of mRNA Human RNAS P." *Science* vol. 263:1267–1273, 1994.

(List continued on next page.)

*Primary Examiner*—John L. Leguyader
*Assistant Examiner*—Sean M Garry
*Attorney, Agent, or Firm*—Arnall Golden & Gregory, LLP

[57] ABSTRACT

External guide sequence (EGS) molecules for eukaryotic RNAse P are engineered to target efficient and specific cleavage of target RNA. Engineered RNA molecules are designed and synthesized which contain specific nucleotide sequences which enable an external guide sequence for RNAse P to preferentially bind to and promote RNAse P-mediated cleavage of target RNA molecules. Short External Guide Sequence (SEGS) molecules have been constructed that, when hybridized to a target molecule, provide a minimal structure recognized as a substrate by RNAse P. The SEGS/target structure is comprised of a structures similar to the A stem and the T stem of a tRNA, the natural substrate of RNAse P. The SEGS makes up only half of these stem structures. The other half of the stem structures is provided by the target molecule. By allowing the target molecule to form more of the RNAse P substrate structure, the disclosed SEGS molecules can be significantly smaller than previous EGS molecules. This makes SEGS molecules especially useful as therapeutic agents since they are easier to manufacture and administer in quantity.

24 Claims, 7 Drawing Sheets

OTHER PUBLICATIONS

Agrawal, et al., "Oligodeoxynucleoside Phpsphoramidates And Phosphorothioates As Inhibitors Of Human Immunodeficiency Virus", *Proc. Natl. Acad. Sci. USA*, 85:7079–7083 (1988).

Altman, "RNA Enzyme–Directed Gene Therapy", Proc. Natl. Acad. Sci. USA, 90:10898–10900 (1993).

Altman, "Ribonuclease P: An Enzyme With A Catalytic RNA Subunit", Advances in Enzymology, Ed., Alton Meister, John Wiley & Sons, 62:1–36 (1989).

Altman, et al., "Catalysis By Ten RNA Subunit Of RNase P—a Minireview" *Gene* 82:63–64 (1989).

Altman, "Ribonuclease P", *J. Biol. Chem.*, 265:20053–20056 (1990).

Baer, et al., "Structure And Transcription Of A Human Gene Fro H1 RNA, The RNA Component Of Human RNase P", *Nucleic Acids Research*, 18:97–103 (1989).

Bartkiewicz, et al., "Identification And Characterization Of An RNA Molecule That Copurifies With RNase P Activity From He la Cells", *Genes Dev.*, 3:488–499 (1989).

Beaudry & Joyce, "Directed Evolution Of An RNA Enzymes", *Science*, 257:635 (1992).

Berzal & Heranz, et al., "In Vitro Selection Of Active Hairpin Ribozymes By Sequential RNA–Catalyzed Cleavage And Ligation Reactions", *Genes And Dev.*, 6:129 (1992).

Branch & Robertson, "A Replication Cycle For Viroids And Other Small Infectious RNA's", *Science*, 233:450–455.

Branch, et al., "An Ultraviolet–Sensitive RNA Structural Element In A Viroid–Like Domain Of The Hepatitis Delta Virus", *Science*, 243:649–652 (1989).

Carrara, et al., "Two Helices Plus A Linker: A Small Model Substrate For Eukaryotic RNas P", *Proc. Natl. Acad. Sci. (USA)*, 92:2627–2631 (1995).

Cech, "Self–Splicing Of Group I Introns", *Annu. Rev. Biochem.*, 59:543–568, (1990).

Chowdhury, et al., "Fate Of DNA Targeted To The Liver By Asialoglycoprotein Receptor–Mediated Endocytosis In Vivo", *J. Biol. Chem.*, 268(15):11265–11271 (1993).

Chowrira, et al., "Novel Guanosine Requirement For Catalysis By The Hairpin Ribozyme", *Nature*, 354:320 (1991).

Clarenc, et al., "Delivery of Antisense Oligonucleotide By Poly(L–lysine) Conjugation And Liposome Encapsulation", *Anti–Cancer Drug Design*, 8(1):81–94 (1993).

Crystal, et al., "Transfer Of Genes To Humans Early Lessons And Obstacles To Success", *Science*, 270:404–410 (1995).

Das, et al., "Upstream Regulatory Elements Are Necessary And Sufficient For Transcription Of A U6 RNA Gene By RNA Polymerase III", *EMBO*, 7:503–512 (1988).

Doerson, et al., "Characterization Of An RNase P Activity From HeLa Cell Mitochondria", *J. Biol. Chem.*, 260:5942 (1985).

Felgner, "Particulate Systems And Polymers For In Vitro And In Vivo Delivery Of Polynucleotide", *Advanced Drug Delivery Reviews*, 5:163–187 (1990).

Felgner, et al. "Lipofection: A Highly Efficient, Lipid–Mediated DNA–Transfection Procedure", *Proc. Natl. Acad. Sci. USA*, 84:7413–7417.

Felgner, et al., "Cationic Liposome–Mediated Transfection", *Nature*, 337:387–388 (1989).

Forster & Altman, "Similar Cage–Shaped Structures For The RNA Components Of All Ribonuclease P And Ribonuclease MRP Enzymes", *Cell*, 62:407–409 (1990).

Forster & Altman, "External Guide Sequences For An RNA Enzyme", *Science*, 249:783–786 (1990).

Forster & Symons, "Self–Cleavage Of Virusoid RNA Is Performed By The Proposed 55–Nucleotide Active Site", *Cell*, 50:9–16 (1987).

Fowlkes & Shenk, "Transcriptional Control Regions Of The Adenovirus VAI RNA Gene", *Cell*, 22:405–413 (1980).

Froehler, et al., "Oligodeoxynucleotides Containing C–5 Propyne Analogs Of 2'–Deoxyuridine And 2'–Deoxycytidine", *Tetrahedron Letters*, 33:5307–5310 (1992).

Fuhrhop, et al., In: Porphyrins and Metalloporphyrins, (K.M. Smith, Ed.) (Elsevier, Amsterdam), 804–807 (1975).

Green, et al., "In Vitro Genetic Analysis Of The Tetrahymena Self–Splicing Intron", *Nature*, 347:406 (1990).

Grigoriev, et al., A Triple Helix–Forming Oligonucleotide–Intercalator Conjugate Acts As A Transcriptional Repressor Via Inhibition Of NF κB Binding To Interleukin–2 Receptor, *J. Biol. Chem.*, 267:3389–3395 (1992).

Guerrier–Takada, et al., "The RNA Moiety Of Ribonuclease P Is The Catalytic Subunit Of The Enzyme", *Cell*, 35:849–857 (1983).

Guerrier–Takada, et al., "Specific Interactions In RNA Enzyme–Substrate Complexes", *Science*, 246:1578–1584 (1989).

Guerrier–Takeda & Altman, "Catalytic Activity Of An RNA Molecuel Prepared By Transcription In Vitro", *Science*, 223:285–286 (1984).

Gupta & Reddy, "Compilation Of Small RNA Sequences", *Nucleic Acids Res.*, 19:2073–2075 (1990).

Hall, et al., "Transcription Initiation Of Eucaryotic Transfer RNA Genes", *Cell*, 29:3–5 (1982).

Hansen, et al., "Physical Mapping And Nucleotide Sequence Of The rnpA Gene That Encodes The Protein Component Of Ribonuclease P In *Escherichia Coli*", *Gene*, 38:85–93 (1985).

Heidenreich & Eckstain, "Hammerhead Ribozyme–Mediated Cleavage Of The Long Terminal Repeat RNA Of Human Immunodeficiency Virus Type 1", *J. Biol. Chem*, 267:1904–1909 (1992).

Hoke, et al., "Effects Of Phosphorothioate Capping On Antisense Oligonucleotide Stability, Hybridization And Antiviral Efficacy Versus Herpes Simplex Virus Infection", *Nucleic Acids Res.*, 19:5743–5748 (1991).

Itakura, et al., "Synthesis And Use Of Synthetic Oligonucleotide", *Ann. Rev. Biochem.*, 53:323–356 (1984).

Johnson & Lloyd–Jones, eds., Drug Delivery Systems (Chichester, England: Ellis Horwood Ltd., (1987).

Johnston, et al., "Present Status And Future Prospects For HIV Therapies", 260:1286–1292 (1993).

Joyce, "Amplification, Mutation And Selection Of Catalytic RNA", *Gene*, 82:83–87 (1989).

Jucker & Pardi, "GNRA Tetraloops Make A U–Turn", *RNA*, 1:219–222 (1995).

Kickoefer, et al., "Vault Ribonucleoprotein particles From Rat And Bullfrog Contain A Related Small RNA That Is Transcribed By RNA Polymerase III", *J. Biol. Chem.*, 268:7868–7873 (1993).

Kim, et al., "Preparation Of Multivesicular Liposomes", *Biochim. Biophys. Acta.* 728:339–348 (1983).

Korba & Gerin, "Use Of A Standardized Cell Culture Assay To Assess Activities Of Nuceloside Analogs Against Hepatitis B Virus Replication", *Antiviral Research*, 19:55–70 (1992).

Kruger, et al., "Self–Splicing RNA: Autoexcision And Autocyclization Of The Ribosomal RNA Intervening Sequence Of Tetrahymena", *Cell*, 31:147–157 (1982).

Kunkel, et al., "U6 Small Nuclear RNA Is Transcribed By RNA Polymerase III", *Proc. Natl. Acad. Sci. USA*, 83:8575–8579 (1987).

Kunkel & Pederson, "Transcription Of A Human U6 Small Nuclear RNA Gene In Vivo Withstands Deletion Of Intragenic Sequences But Not Of An Upstream TATATA Box", *Nucleic Acids Res.*, 18:7371–7379 (1989).

*Lawrence & Altman, "Site–Directed Mutagenesis Of M1 RNA Subunit Of *Escherichia Coli* Ribonuclease P", *J. Mol. Biol.*, 191:163–175 (1986).

Lee, et al., "Recognition Of Liposomes By Cells: In Vitro Binding And Endocytosis Mediated By Specific Lipid Headgroups And Surface Charge Density", *Biochem. Biophys. Acta.*, 1103:185–197 (1992).

Lee, et al., "Partial Characterization Of An RNA Component That Copurifies With *Saccharomyces Cerevisiae* RNase P", *Molecular And Cellular Biology*, 9(6):2536–2543 (1989).

Leonetti, et al., "Antibody–targeted Liposomes Containing Oligodeoxyribonucleotides Complementary to Viral RNA Selectively Inhibit Viral Replication", *Proc. Natl. Acad. Sci. USA*, 87:2448–2451 (1990).

Leserman, et al., "Targeted Liposomes and Intracellular Delivery of Macromolecules", *Horizons in Membrane Biotechnology*, 95–102 (1990).

Liu, et al., "Role Of Liposome Size And RES Blockade in Controlling Biodistribution And Tumor Uptake Of GM–containing Liposomes", *Biochem. Biophys. Acta*, 1104:95–101 (1992).

Li, et al., "Targeted Cleavage Of mRNA In Vitro By P From *Escherichia Coli*", *Proc. Natl. Acad.*, 89:3185–3189 (1992).

Machy, et al., "Interferon Sensitive and Insensitive MHC Variants of a Murine Thymoma Differentially Resistant to Methotrexate–Containing Antibody–Directed Liposomes and Immunotoxin", *J. Immunology*, 136(8):3110–3115 (1986).

Machy, et al., "Elimination or Rescue of Cells in Culture by Specifically Targeted Liposomes Containing Methotrexate or Formyl–Tetrahydrofolate", *EMBO Journal*, 3(9):1971–1977 (1984).

Maher, et al., "Inhibition Of DNA Binding Proteins By Oligonucleotide–Directed Triple Helix Formation", *Science*, 245:725–730 (1989).

McClain, et al., "Model Substrates For An RNA Enzyme", *Science*, 238:527–530 (1987).

Milhaud, P.G., et al., "Antibody Targeted Liposomes Containing Poly(rI)•poly(rC) Exert a Specific Antiviral and Toxic Effect on Cells Primed with Inferferons α/β or Y", *Biochimica et Biophysica Acta*, 987:15–20 (1989).

Milhaud, et al., "Free and Liposome–Encapsulated Double–Stranded RNAs as Inducers of Interferon, Interleukin–6, and Cellular Toxicity", *J. of Interferon Res.*, 11(1):261–265 (1991).

Milligan, et al., "Oligoribonucleotide Synthesis Using T7 RNA Polymerase And Synthetic DNA Templates", *Nucl Acids Res.*, 15:8783 (1987).

Mills, et al., "Qβ Replicase: Mapping The Functional Domains Of An RNA–Dependent RNA Polymerase", *J. Molecular Biology*,205:751–764 (1988).

Mulligan, "The Basic Science Of Gene Therapy", *Science*, 260:926–932 (1993).

Narang, et al., "Chemical Synthesis Of Deoxyoligonucleotides By The Modified Triester Method", *Methods Enzymol.*, 65:610–620 (1980).

Nielsen, et al., "Transcription Of Human 5S rRNA Genes Is Influenced By An Upstream DNA Sequence", *Nucleic Acids Res.*, 21:3631–3636 (1993).

Noé, et al., "Inhibition of Cell Proliferation with Antibody–Targeted Liposomes Containing Methotrexate–Y–Dimyristoylphosphatidylethanolamine", *Biochimica et Biophysica Acta*, 946:253–260 (1988).

Noonberg, et al., "In Vivo Generation Of Highly Abundant Sequence–Specific Oligonucleotide For Antisense And Triplex Gene Regulation", *Nucleic Acids Res.*, 22:2830–2836 (1995).

Offensperger, et. al., "In Vivo Inhibition Of Duck Hepatitis B Virus Replication And Gene Expression By Phosphorothioate Modified Antisense Oligodeoxynucleotides", *EMBO J.*, 12:1257–1262 (1993).

Ogilvie, et al., "Total Chemical Synthesis Of A 77–Nucleotide–Long RNA Sequence Having Methionine–Acceptance Activity", *Proc. Natl. Acad. Sci. U.S.A.*, 85:5764–5768 (1988).

Orson, et al., "Oligonucleotide Inhibition Of IL2Rα mRNA Transcription by Promoter Region Collinear Triplex Formation In Lymphocytes", *Nucl. Acids Res.*, 19:3435–3441 (1991).

Pace, et al., "Phylogentic Comparative Analysis And The Secondary Of Ribonuclease P RNA — A Review", *Gene*, 82:65–75 (1989).

*Pace, et al., "Ribonuclease P: Function And Variation", *J. Of Biol. Chem.*, 265(7):3587–3590 (1990).

Pan, et al., "Folding Of Circularly Permuted Transfer RNAs", *Science*, 254:1361–1364 (1991).

Paolella, et al., "Nuclease Resistant Ribozymes With High Catalytic Activity", *EMBO J.*, 11:1913–1919 (1992).

Perreault & Altman, "Important 2'–hydroxyl Groups In Model Substrates For M1 RNA. The Catalytic RNA Subunit Of RNase P From *Escherichia Coli*", *J. Mol. Biol.*, 226:399–409 (1992).

Pieken, et al., "Kinetic Characterization Of Ribonuclease–Resistant 2'–Modified Hammerhead Ribozymes", *Science*, 253:314–317 (1991).

Pyle, et al., "Direct Measurement Of Oligonucleotide Substrate Binding To Wild–Type And Mutant Ribozymes From Tetrahymena", *Proc. Natl. Acad. Sci. USA*, 87:8187–8191 (1990).

Quigley & Rich, "Structural Domains Of Transfer RNA Molecules: The Ribose 2' Hydroxyl Which Distinguishes RNA From DNA Plays A Key Role In Stabilizing tRNA Structure", *Science*, 194:796–806 (1976).

R.R.C. New (ed.) "Liposomes: A Practical Approach", IRL Press. Oxford, 179–180 (1992).

Reddy, et al., "The Capped U6 Small Nuclear RNA Is Transcribed By RNA Polymerase III", *J. Biol. Chem.*, 262:75–81 (1987).

Roizman, "The Structure And Isomerization Of Herpes Simplex Virus Genomes", *Cell*, 16:481–494 (1979).

Romero & Blackburn, "A Conserved Secondary Structure For Telomerase RNA", *Cell*, 67:343–353 (1991).

Rossi, et al., "Exploring The Use Of Antisense, Enzymatic RNA Molecules (Ribozymes) As Therapeutic Agents", *Antisense Res. Dev.*, 1:285–288 (1991).

*Rossi, et al., J. Cell Biol. (Supp. 14A D428) (1990).

Sampson, et al., "Characterization Of Two RNA–Catalyzed RNA Cleavage Reactions", *Cold Spring Harbor Sym. Quant. Biol.*, 52:267–275 (1987).

Sarin, et al., "Inhibition Of Acquired Immunodeficiency Syndrome Virus By Oligodeoxynucleoside Methyphosphonates", *Proc. Natl. Acad. Sci. USA*, 85:7448–7794 (1989).

Sarver, et al., "Ribozymes As Potential Anti–HIV–1 Therapeutic Agents", *Science*, 247:1222–1225 (1990).

Scaringe, et al., "Chemical Synthesis Of Biologically Active Oligoribonucleotides Using β–Cyanoethyl Protected Ribonucleoside Phosphoramidites", *Nucleic Acids Research*, 18:5433–5441 (1990).

Seela & Kaiser, "Oligodeoxyribonucleotides Containing 1,3–Propanediol As Nucleoside Substitute", *Nucleic Acids Res.*, 15:3113–3129 (1987).

Sells, et al., (1987) Production Of Hepatitis B Virus Particles In HepG2 Cells Transfected With Cloned Hepatitis B Virus DNA, *Proc. Natl. Acad. Sci. USA*, 84:1005–1009).

Shaw, et al., "Modified Deoxyoligonucleotides Stable To exonuclease Degradation In Serum", *Nucleic Acids Res.*, 19:747–750 (1991).

Suzuki, et al., "CD4 and CD7 Molecules as Targets for Drug Delivery from Antibody Bearing Liposomes", *Exp. Cell Res.*, 193(1):112–119 (1991).

Symons, "Small Catalytic RNAs", *Annu. Rev. Biochem.*, 61:641–671 (1992).

Thierry & Dritschilo, "Intracellular Availability Of Unmodified Phosphorothioated And Liposomally Encapsulated Oligodeoxynucleotides For Antisense Activity", *Nucl. Acids Res.*, 20:5691–5698 (1992).

Thierry, et al., "Multidrug Resistance in Chinese Hamster Cells: Effect of Liposome–Encapsulated Doxorubicin", *Cancer Communications*, 1(5):311–316 (1989).

Thierry, A.R., et al., "Overcoming Multidrug Resistance in Human Tumor Cells Using Free and Liposomally Encapsulated Antisense Oligodeoxynucleotides", *Biochem. Biophys. Res. Comm.*, 190(3):952–962 (1993).

Thompson, et al., "Improved Accumulation And Activity Of Ribozymes Expressed From A tRNA–Based RNA Polymerase III Promoter", *Nucleic Acids Res.*, 23:2259–2268 (1995).

Truneh, et al., "A Calmodulin Antagonist Increases the Apparent Rate of Endocytosis of Liposomes Bound to MHC Molecules Via Monoclonal Antibodies", *Exp. Cell Res.*, 155:50–63 (1984).

Uhlenbeck, "A Small Catalitc Oligoribonucleotide", *Nature*, 328:596–600 (1987).

Wang, et al., "Highly Efficient DNA Delivery Delivery Mediated By ph–Sensitive Immunoliposomes", *Biochem.*, 28:9508–9514 (1989).

Whitton, "Antisens Treatment Of Viral Infection", *Adv. Viral Res.*, 44:267–303 (1994).

Yuan, et al., "Trageted Cleavage Of mRNA By Human RNase P", *Proc. Natl. Acad. Sci. USA*, 89:8006–8010 (1992).

Yuan & Altman, "Substrate Recognition By Human RNase P: Identification Of Small, Model Substrates For The Enzyme", *EMBO J*, 14:159–168 (1995).

Zhu, et al., "Systemic Gene Expression After Intravenous DNA Delivery Into Adult Mice", *Science*, 261:209–211 (1993).

GCA CGG AAU UCG GUG GGG CCA GCU CCU GAA GGU UCG AAA
AAA A        43 nucleotides

AAU CCU UCC CCC ACC                            15 nucleotides

GGC UCA GUU UAC UAG UGC CAU UUG UUC AGU GGU UCG
36 nucleotides

AAU CCA CUG CAC UAG                            15 nucleotides

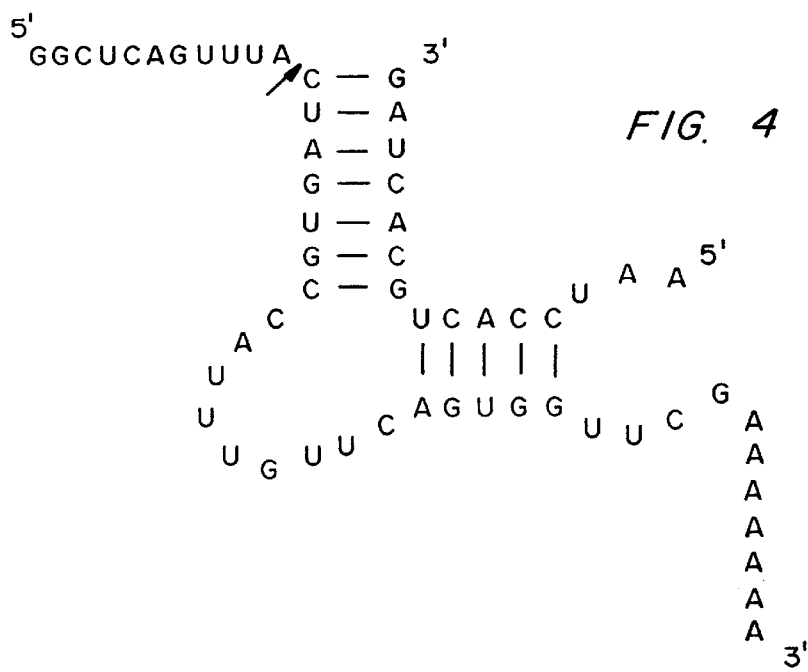
FIG. 4
GGC UCA GUU UAC UAG UGC CAU UUG UUC AGU GGU UCG AAA
AAA A    43 nucleotides
AAU CCA CUG CAC UAG            15 nucleotides
FIG. 5
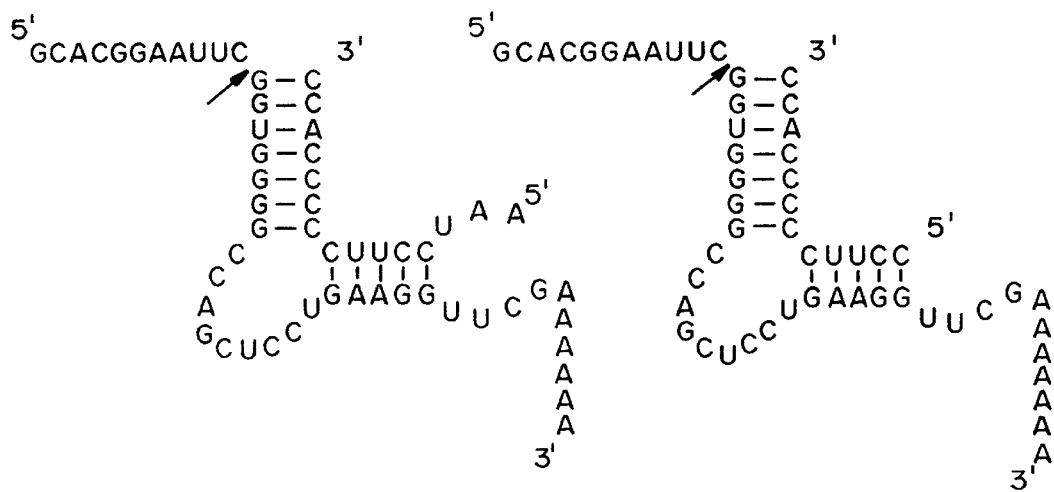
15 nucleotide EGS        12 nucleotide EGS GGC UCA GUU UAC UAG UGC CAU UUG UUC AGU GGU UCG AAU
CCA CUG CAC UAG           51 nucleotides GCA CGG AAU UCG GUG GGG CCA GCU CCU GAA GGU
UCG AAU CCU UCC CCC ACC          51 nucleotides GCA CGG AAU UCG GUG GGG CCA GCU CCU GAA GGU UCG
36 nucleotides AAU CCU UCC CCC ACC                              15 nucleotides

SHORT EXTERNAL GUIDE SEQUENCES

BACKGROUND OF THE INVENTION

This application is directed to methods and external guide sequence compositions designed to target cleavage of RNA by RNAse P.

Ribonucleic acid (RNA) molecules can serve not only as carriers of genetic information, for example, genomic retroviral RNA and messenger RNA (mRNA) molecules and as structures essential for protein synthesis, for example, transfer RNA (tRNA) and ribosomal RNA (rRNA) molecules, but also as enzymes which specifically cleave nucleic acid molecules. Such catalytic RNA molecules are called ribozymes.

The discovery of catalytic RNA, by Drs. Altman and Cech, who were awarded the Nobel prize in 1989, has generated much interest in commercial applications, particularly in therapeutics (Altman, *Proc. Natl. Acad. Sci. USA* 90:10898–10900 (1993); Symons, *Annu. Rev. Biochem.* 61:641–671 (1992); Rossi et al., *Antisense Res. Dev.,* 1:285–288 (1991); Cech, *Annu. Rev. Biochem.* 59:543–568, (1990)). Several classes of catalytic RNAs (ribozymes) have been described, including intron-derived ribozymes (WO 88/04300; see also, Cech, T., *Annu. Rev. Biochem.,* 59:543–568, (1990)), hammerhead ribozymes (WO 89/05852 and EP 321021 by GeneShears), axehead ribozymes (WO 91/04319 and WO 91/04324 by Innovir).

RNAse P

Another class of ribozymes include the RNA portion of an enzyme, RNAse P, which is involved in the processing of transfer RNA (tRNA), a common cellular component of the protein synthesis machinery. Bacterial RNAse P includes two components, a protein (C5) and an RNA (M1). Sidney Altman and his coworkers demonstrated that the M1 RNA is capable of functioning just like the complete enzyme, showing that in *Escherichia coli* the RNA is essentially the catalytic component, (Guerrier-Takada et al., Cell 35:849–857 (1983)). In subsequent work, Dr. Altman and colleagues developed a method for converting virtually any RNA sequence into a substrate for bacterial RNAse P by using an external guide sequence (EGS), having at its 5' terminus at least seven nucleotides complementary to the nucleotides 3' to the cleavage site in the RNA to be cleaved and at its 5' terminus the nucleotides NCCA (N is any nucleotide)(WO 92/03566 by Yale, and Forster and Altman, *Science* 238:407–409 (1990)).

Using similar principles, EGS/RNAse P-directed cleavage of RNA has been developed for use in eukaryotic systems, where the external guide sequence forms structures similar to the stem and loop structures of tRNA and where the substrate RNA hybridizes to ends of the EGS to form structures similar to the acceptor and D stems of tRNA (Yuan et al., *Proc. Natl. Acad. Sci. USA* 89:8006–8010 (1992); WO 93/22434 by Yale). It has subsequently been shown that EGS molecules for use with eukaryotic RNAse P need form only a structure similar to the T stem and loop of tRNA, where, again, the substrate RNA hybridizes to ends of the EGS to form structures similar to the acceptor and D stems of tRNA (WO 95/24489 to Yale). These EGS molecules are useful for promoting RNAse P-mediated cleavage of target RNA molecules. They are especially useful for in vivo use since only the relatively small EGS molecule need be administered. The catalytic RNAse P is already present and active in the cells of the animal or patient. Yuan and Altman, *EMBO J* 14:159–168 (1995), and Carrara et al., *Proc. Natl. Acad. Sci.* (USA) 92:2627–2631 (1995), later determined a minimal structure necessary for cleavage of a substrate by RNase P.

It is an object of the present invention to provide a therapeutic targeted for treatment of viral diseases and diseases involving abnormal transcription products, and method of use thereof.

It is another object of the present invention to provide short external guide sequences for RNase P, vectors encoding such short external guide sequences, and methods of use thereof.

It is another object of the present invention to provide chemically modified short external guide sequences for RNAse P with enhanced resistance to nuclease degradation.

It is another object of the present invention to provide methods of cleaving target RNA molecules promoted by short external guide sequences for RNAse P.

It is a further object of the present invention to provide short external guide sequences for RNAse P specifically targeted against viruses such as hepatitis, vectors encoding such short external guide sequences, and methods of use thereof.

SUMMARY OF THE INVENTION

External guide sequence (EGS) molecules for eukaryotic RNAse P are engineered to target efficient and specific cleavage of target RNA. They contain specific nucleotide sequences which enable an external guide sequence for RNAse P to preferentially bind to and promote RNAse P-mediated cleavage of target RNA molecules. Short External Guide Sequence (SEGS) molecules have been constructed that, when hybridized to a target molecule, provide a minimal structure recognized as a substrate by RNAse P. The small EGS/target structure includes structures similar to the A stem and the T stem of a tRNA, the natural substrate of RNAse P. The SEGS makes up only half of these stem structures. The other half of the stem structures is provided by the target molecule. By allowing the target molecule to form more of the RNAse P substrate structure, the disclosed SEGS molecules can be significantly smaller than previous EGS molecules. This makes SEGS molecules especially useful as therapeutic agents since they are easier and less expensive to manufacture and administer in quantity.

Chemically modified versions of these SEGS molecules having modified nucleotides or nucleotide linkages are designed to enhance their resistance to nuclease degradation. Specific regions are modified to achieve enhanced stability while maintaining RNAse P targeting activity. Examples demonstrate that SEGS molecules for RNAse P have been constructed that bind to and promote RNAse P cleavage of hepatitis viral RNA. Methods for the determination of the activity of an SEGS, for the purpose of construct-screening, as well as methods for using and producing such RNA molecules, are also disclosed.

BRIEF DESCRIPTION OF THE DRAWINGS

FIG. 4 is a diagram of the structure of EGS a with the nucleotide sequence SEQ ID NO.3 and a short model target RNA (T a') with the nucleotide sequence SEQ ID NO.4. The two oligonucleotides are aligned to show the base pairing which forms a structure similar to the A stem and T stem of tRNA. This structure is recognized by eukaryotic RNAse P and promotes RNAse P-mediated cleavage of the target RNA. The RNAse P cleavage site is indicated with an arrow. The model target RNA matches a portion of HBV sequence.

FIG. 5 is a diagram of RNAse P cleavage reactions resolved on a polyacrylamide gel involving a 15 nucleotide SEGS and a 12 nucleotide SEGS and structures of the SEGS and substrate involved. In the diagram, – indicates that no RNAse P was present in the reaction and + indicates that RNAse P was present. On the bottom left is shown the structure of the 15 nucleotide SEGS (EGS 3; SEQ ID NO. 1) hybridized to the short model target RNA (T 7; SEQ ID NO. 2). On the bottom right is shown the structure of the 12 nucleotide SEGS (EGS 7; nucleotides 4 to 15 of SEQ ID NO. 1) hybridized to the short model target RNA (T 7; SEQ ID NO. 2). The structures are shown beneath the pair of lanes showing the RNAse P reactions in which these oligonucleotides were involved. The SEGS and target RNA are aligned to show the base pairing which forms a structure similar to the A stem and T stem of tRNA. This structure is recognized by eukaryotic RNAse P and promotes RNAse P-mediated cleavage of the target RNA. The RNAse P cleavage site is indicated with an arrow.

DETAILED DESCRIPTION OF THE INVENTION

Oligonucleotides suitable for promoting cleavage of target RNA molecules have been constructed. The oligonucleotides are external guide sequence (EGS) molecules for eukaryotic RNAse P which are designed to specifically bind to and promote RNAse P-mediated cleavage of target RNA molecules and to have enhanced nuclease resistance. These EGS molecules differ in structure and size from previous external guide sequences, and are referred to as Short External Guide Sequence (SEGS). A key distinguishing characteristic is that SEGS do not, by themselves, form a structure similar to the T stem and loop of tRNA.

SEGS suitable for use in the treatment of hepatitis B viral infections have been constructed. As used herein, "external guide sequence" and "EGS" refer to any oligonucleotide that forms an active cleavage site for RNAse P in a target RNA. "Short External Guide Sequence" and "SEGS" refer to the short forms of EGS described below. The terms "Short External Guide Sequence" and "SEGS" are intended to refer only to the short forms of EGS molecules as described below rather than "short" EGS molecules in general, that is, EGS molecules which are merely "short." To emphasize this distinction, "Short External Guide Sequence" is capitalized herein. Where reference is made herein to external guide sequences it is intended that SEGS are encompassed.

Figure 1:
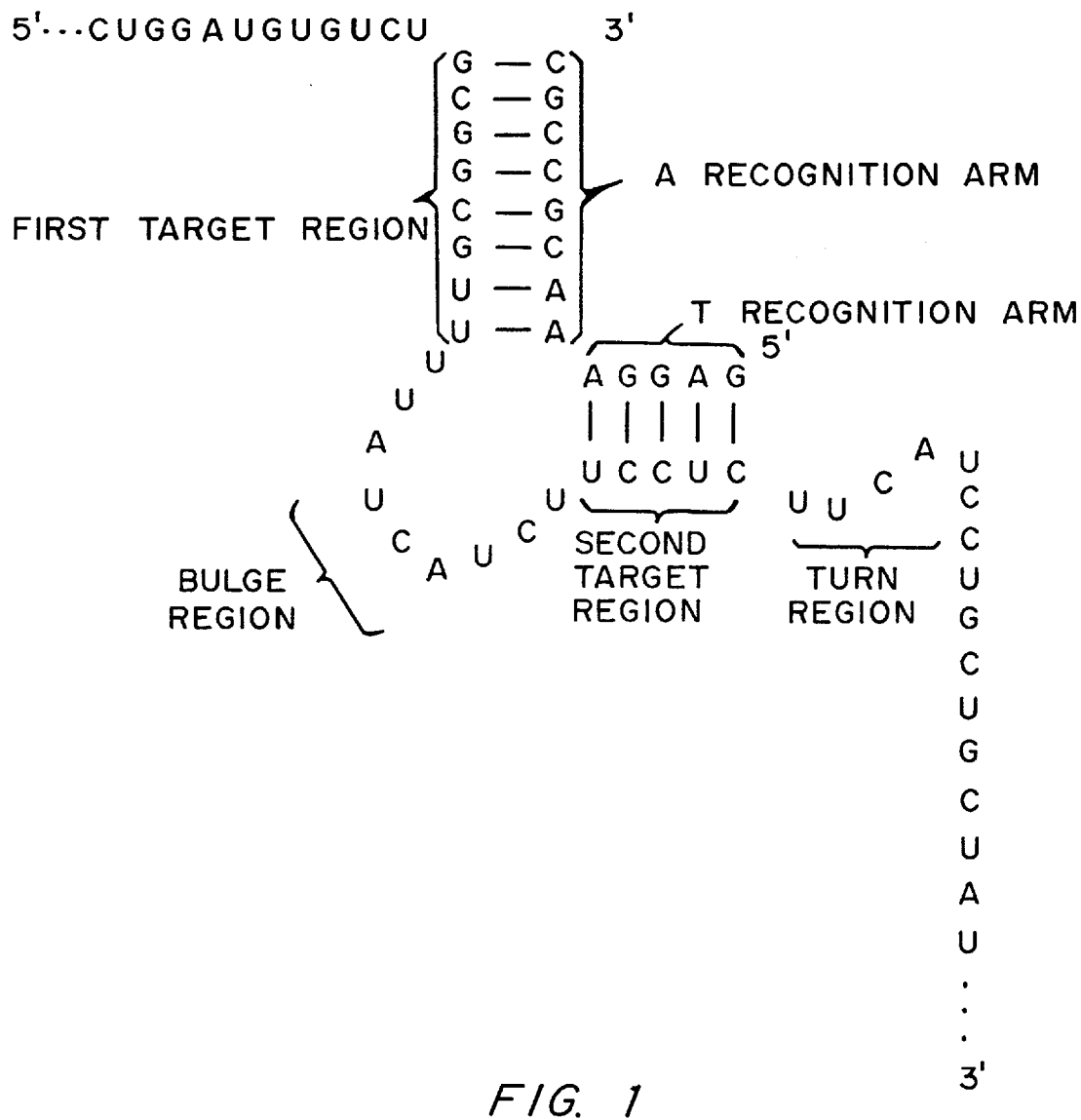
FIG. 1 is a diagram of the structure of a Short External Guide Sequence (SEGS) hybridized to a target RNA molecule. The parts of the SEGS (SEQ ID NO. 6) and target RNA molecule (SEQ ID NO. 7), with each serving a specific structural role in the SEGS/target RNA complex. The parts of the SEGS are, from 5' to 3', the T recognition arm and the A recognition arm. The parts of the target RNA are, from 5' to 3', the first target region, the bulge region, the second target region, and the turn region. The primary structural relationship between the SEGS and the target RNA is that the A recognition arm is complementary to the first target region and the T recognition arm is complementary to the second target region. Except for two of the nucleotides in the turn region, the sequences shown are merely examples and are not critical to obtaining RNAse P-mediated cleavage of target RNA in general. In this example, the target RNA is HBV RNA.

Previous EGS molecules were designed to form a structure similar to at least the T stem and loop of tRNA, with a 3' tail and 5' tail which hybridize to a target RNA molecule to form structures similar to the A stem and D stem of tRNA. It has been discovered that the structures similar to the T loop and D stem are unnecessary for cleavage of a target RNA/EGS structure. In the disclosed Short External Guide Sequence molecules, the SEGS and target RNA molecule together form structures similar to the A stem and T stem of tRNA. Unlike previous EGS molecules, a SEGS does not form a T loop and does not, by itself, form a structure similar to a T stem. Instead, the target RNA molecule hybridizes to the SEGS to form half of a structure similar to the T stem of tRNA. An example of a SEGS hybridized to its target RNA molecule is shown in FIG. 1.

SEGS are distinguished from previous EGS molecules in that 1) there is no intact T loop, 2) the SEGS and target RNA do not form a structure similar to the D stem of tRNA, and 3) the target RNA, in combination with the SEGS, forms half of a structure similar to the T stem of tRNA.

SEGS have several advantages over previous EGS molecules. 1) They are easier to synthesize and purify SEGS, and they will cost less, due to their shorter length, 2) the use of the T stem for target recognition will impart more specificity to the EGS since the short D stems used for target recognition in previous EGS molecules provide less target-specific sequence in the EGS, thereby decreasing the specificity of cleavage, and 3) a SEGS will be taken up by the cell more readily.

I. Design and Synthesis of SEGS Molecules

SEGS molecules are synthetic oligonucleotides that bind to a target substrate to form a secondary and tertiary structure resembling the natural cleavage site of precursor tRNA for eukaryotic RNAse P. The ability of SEGS molecules to target and promote RNAse P activity is readily determined using an in vitro activity assay for cleavage by RNAse P of a target RNA sequence, as described in more detail below. In the case of SEGS molecules with modified nucleotides or nucleotide linkages, a stability assay allows determination of the nuclease resistance of various types of modification. The activity assay permits comparison of the efficiency of RNAse P-mediated cleavage promoted by SEGS molecules with different modifications. Together, the assays are used to optimize and balance stability and cleavage efficiency of modified SEGS molecules.

Exemplary SEGS molecules have been constructed which are suitable for use in the treatment of viral disease. The specific target is the hepatitis B virus, more particularly, the hepatitis B surface antigen (HBsAg) encoding RNA. Since HBsAg plays an essential role in viral suprastructure and infection, SEGS-based therapeutics can be used to down-regulate hepatitis through cleavage of HBsAg mRNA. Preferred targeted sites within hepatitis B RNA, or other target RNAs, are regions of conserved sequence which appear in all forms of the target RNA and which have a UNR motif as described below. Five such preferred sites have been identified in the HBsAg encoding region of hepatitis B RNA and are targeted by SEGS molecules having nucleotide base sequences shown in SEQ ID NO. 6, SEQ ID NO. 8, SEQ ID NO. 10, SEQ ID NO. 12, and SEQ ID NO. 14.

A. Design of SEGS Molecules

SEGS molecules can be designed by adapting a portion of the basic structure of a pre-tRNA molecule to form a substrate recognition sequence. This recognition sequence is complementary to regions of a targeted sequence in a target RNA molecule. In SEGS, the recognition sequence is composed of two recognition arms, referred to as the A recognition arm and the T recognition arm, which, in combination with regions of the targeted sequence in the target RNA, form structures similar to the A stem and T stem, respectively, of a tRNA molecule. The T recognition arm is located 5' of and adjacent to the A recognition arm. The sequence of the recognition arms are chosen to be specifically complementary to two regions of the targeted sequence in the target RNA, referred to as the first target region and the second target region. The first target region encompasses, or is adjacent to and 3' of, the site where RNAse P-mediated cleavage occurs.

The sequences of the recognition arms are chosen such that the first and second target regions in the target RNA are separated by a short unpaired region, referred to as the bulge region. Formation of this structure is the only essential requirement for defining the nucleotide sequence of a SEGS. However, it is preferred that the sequences of the recognition arms are also chosen such that a UNR motif is present in the target RNA molecule adjacent to and 3' of the second target region. The UNR motif can be immediately adjacent to the second target region, or it may be separated from the second target region by one or a few spacer nucleotides. It is preferred that the UNR motif is separated from the second target region by from zero to ten spacer nucleotides, more preferred that the UNR motif is separated from the second target region by from zero to three spacer nucleotides, and most preferred that the UNR motif is separated from the second target region by one spacer nucleotide. The UNR motif has a nucleotide sequence of UNR where N represents any nucleotide, R represents any purine nucleotide, and U represents a uridine nucleotide. The region of the targeted sequence in the target RNA molecule that makes up the UNR motif, if present, and spacer nucleotides is referred to as the turn region. The turn region, if present, is immediately adjacent to and 3' of the second target region. Without wishing to be limited by any particular theory, it is believed that the potential of the turn region of the targeted sequence in a target RNA to form a uridine turn structure (see Quigley and Rich, *Science* 194:796–806 (1976), and Junker and Pardi, *RNA* 1:219–222 (1995)) aids in promoting RNAse P-mediated cleavage of the target RNA.

According to the relationships described above, the targeted sequence in the target RNA is composed of, from 5' to 3', the first target region, the bulge region, and the second target region, where the A recognition arm of the SEGS is complementary to the first target region and the T recognition arm of the SEGS is complementary to the second target region. It is preferred that a turn region, having a UNR motif, is also present in the targeted sequence 3' of the second target region. An example of these regions and relationships are shown in FIG. 1.

The recognition arms can be any length that results in a functional SEGS molecule. It is preferred that the A recognition arm and T recognition arm together total from 12 to 16 nucleotides. It is most preferred that the A recognition arm and T recognition arm together total 12 or 13 nucleotides. In general, it is preferred that the A recognition arm be from seven to nine nucleotides long, and that the T recognition arm be from five to seven nucleotides long. It is most preferred that the A recognition arm be seven or eight nucleotides long and the T recognition arm be five or six nucleotides long. In general, the recognition arms can have any nucleotide sequence. As discussed below, the choice of sequence is preferably based on the sequence of targeted sequence in a target RNA of interest. It is preferred that the nucleotide at the 3' end of the A recognition arm is a cytidine or guanidine nucleotide. It is most preferred that the nucleotide at the 3' end of the A recognition arm is a cytidine nucleotide.

The bulge region can be any length that results in a functional SEGS molecule. It is preferred that the bulge region be from 1 to 30 nucleotides long. It is more preferred that the bulge region be from five to fifteen nucleotides long. It is most preferred that the bulge region be nine nucleotides long. The turn region, if present, can have any sequence that includes the consensus formula UNR that results in a functional SEGS molecule, where N represents any nucleotide, R represents any purine nucleotide, and U represents a uridine nucleotide. It is preferred that the turn region has a sequence of NUNR. It is more preferred that the turn region has a sequence of NUCR or UUNR. It is most preferred that the turn region has a sequence of UUCR.

Functional SEGS molecules require only that they form, in combination with a target RNA, a structure corresponding to the A stem and T stem of precursor tRNA such that an unpaired region is present in the target RNA between the structures corresponding to the A stem and T stem of tRNA. No structure corresponding to the T loop of a tRNA is required. Thus, a functional SEGS molecule requires only a nucleotide sequence complementary to two regions of the target RNA molecule, where the regions of the target RNA molecule are separated by a region, the bulge region, that is not complementary to the SEGS. It is preferred that a turn region containing a UNR motif is also present in the target RNA adjacent to and 3' of the structure corresponding to the T stem of tRNA.

SEGS can be designed to target any sequence in any target RNA of interest. However, SEGS are preferably designed by searching the nucleotide sequence of a target RNA of interest for the location of UNR motifs. For more preferred SEGS, the search can be limited to the preferred sequences of turn regions as described above. Once a UNR motif is identified, the sequence of the T recognition arm of the SEGS is chosen to be complementary to nucleotides in the target RNA adjacent to and 5' of the UNR motif, separated by one or a few spacer nucleotides, if desired. These nucleotides in the target RNA represent the second target region. The sequence of the A recognition arm of the SEGS is chosen to be complementary to nucleotides in the target RNA 5' of the second target region, separated by an unpaired region. The unpaired region is the bulge region in the targeted sequence.

Figure 7:
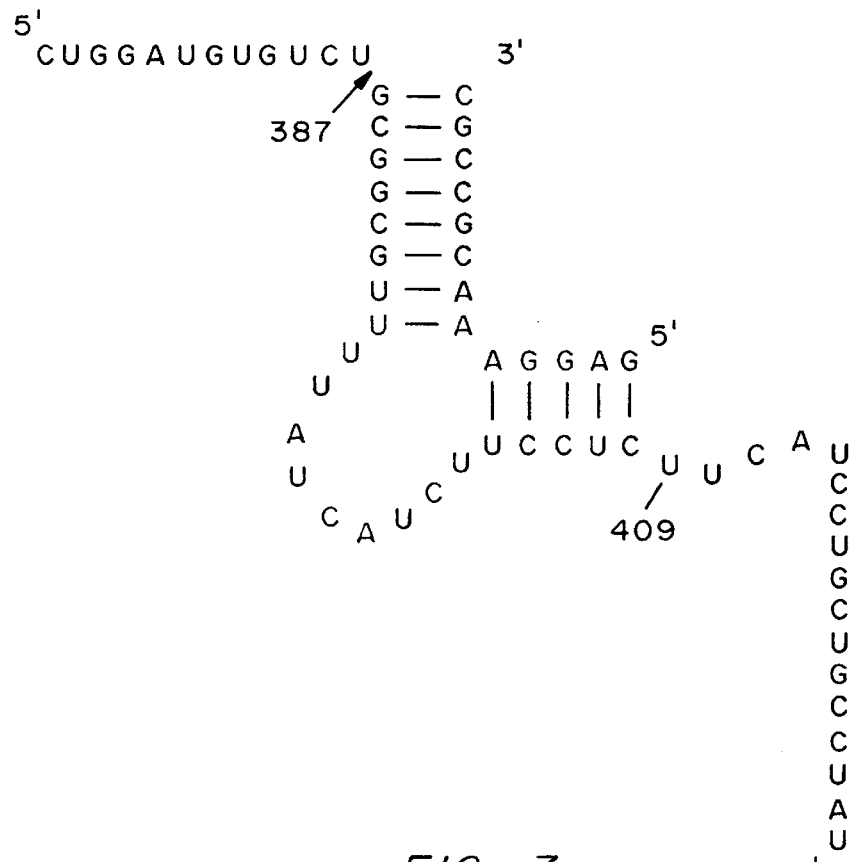
FIG. 7 is a diagram of the structure formed by hybridization of a SEGS (HBV B) with the nucleotide sequence SEQ ID NO. 6 to a portion HBV RNA corresponding to nucleotides 375–424 of a 2.1 kb HBV RNA (SEQ ID NO. 7). The SEGS and HBV RNA are aligned to show the base pairing which forms a structure similar to the A stem and T stem of tRNA. The RNAse P cleavage site is indicated with an arrow.
Figure 8:
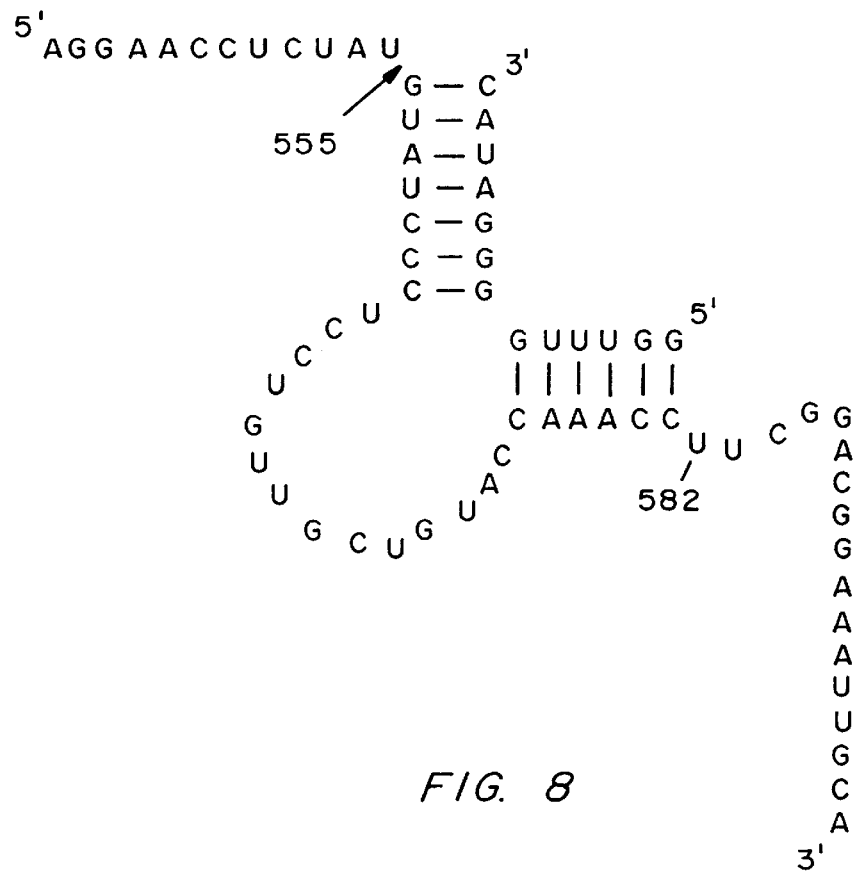
FIG. 8 is a diagram of the structure formed by hybridization of a SEGS (HBV C) with the nucleotide sequence SEQ ID NO. 8 to a portion HBV RNA corresponding to nucleotides 543–598 of a 2.1 kb HBV RNA (SEQ ID NO. 9). The SEGS and HBV RNA are aligned to show the base pairing which forms a structure similar to the A stem and T stem of tRNA. The RNAse P cleavage site is indicated with an arrow.
Figure 9:
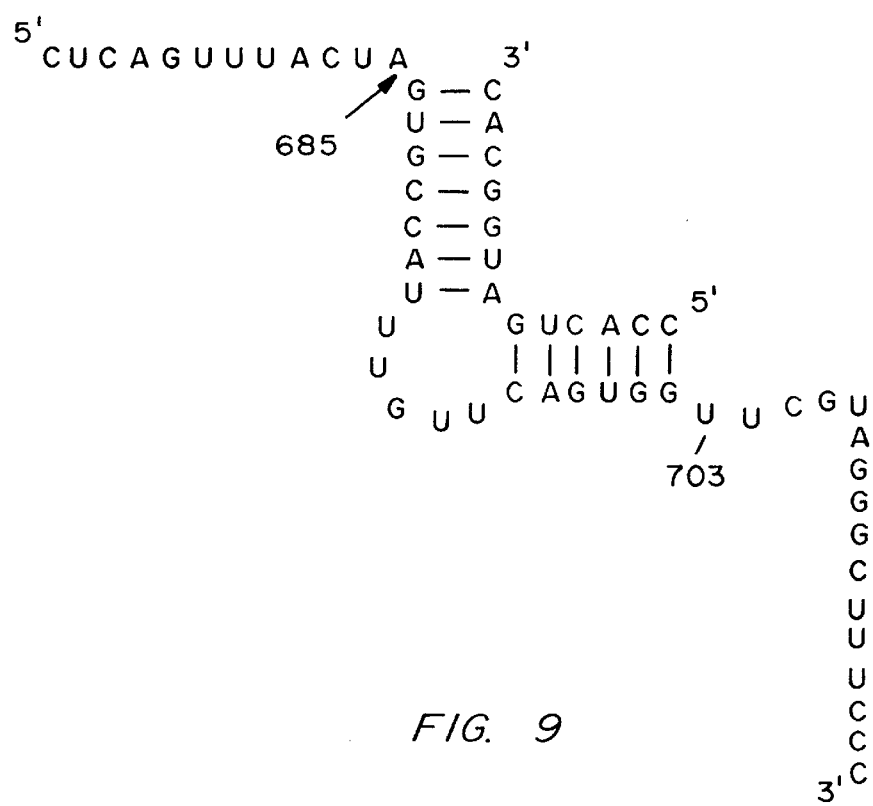
FIG. 9 is a diagram of the structure formed by hybridization of a SEGS (HBV F1) with the nucleotide sequence SEQ ID NO. 10 to a portion HBV RNA corresponding to nucleotides 673–718 of a 2.1 kb HBV RNA (SEQ ID NO. 11). The SEGS and HBV RNA are aligned to show the base pairing which forms a structure similar to the A stem and T stem of tRNA. The RNAse P cleavage site is indicated with an arrow.
Figure 10:
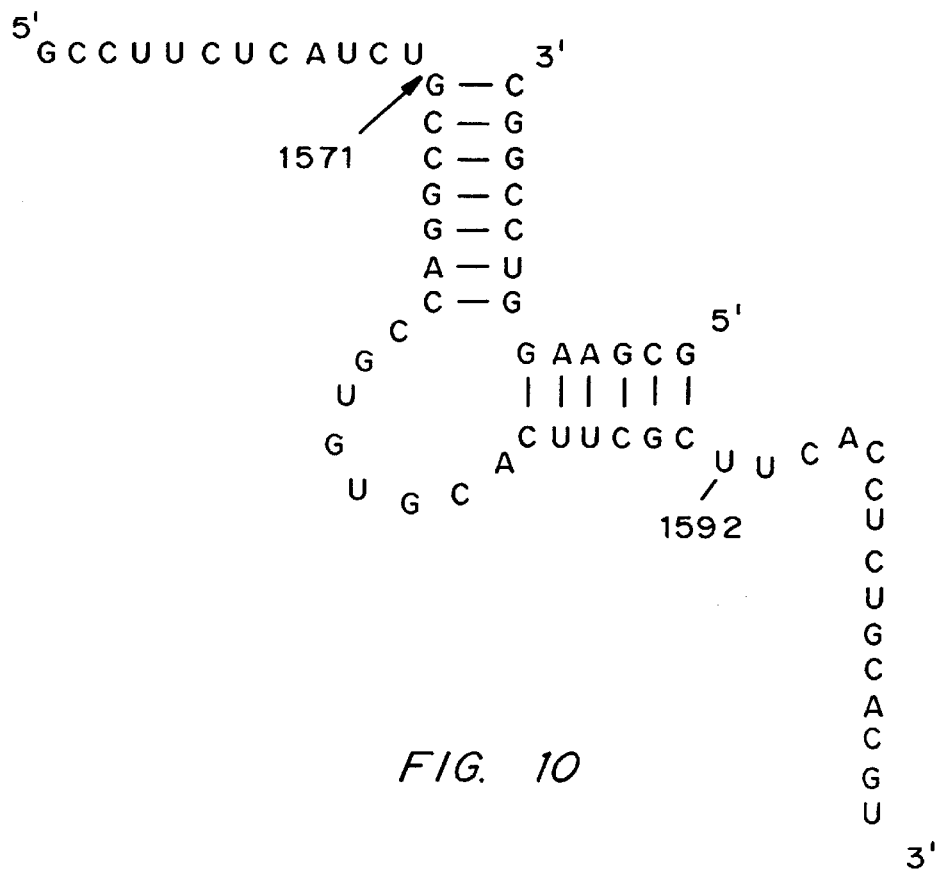
FIG. 10 is a diagram of the structure formed by hybridization of a SEGS (HBV H) with the nucleotide sequence SEQ ID NO. 12 to a portion HBV RNA corresponding to nucleotides 1559–1606 of a 2.1 kb HBV RNA (SEQ ID NO. 13). The SEGS and HBV RNA are aligned to show the base pairing which forms a structure similar to the A stem and T stem of tRNA. The RNAse P cleavage site is indicated with an arrow.
Figure 11:
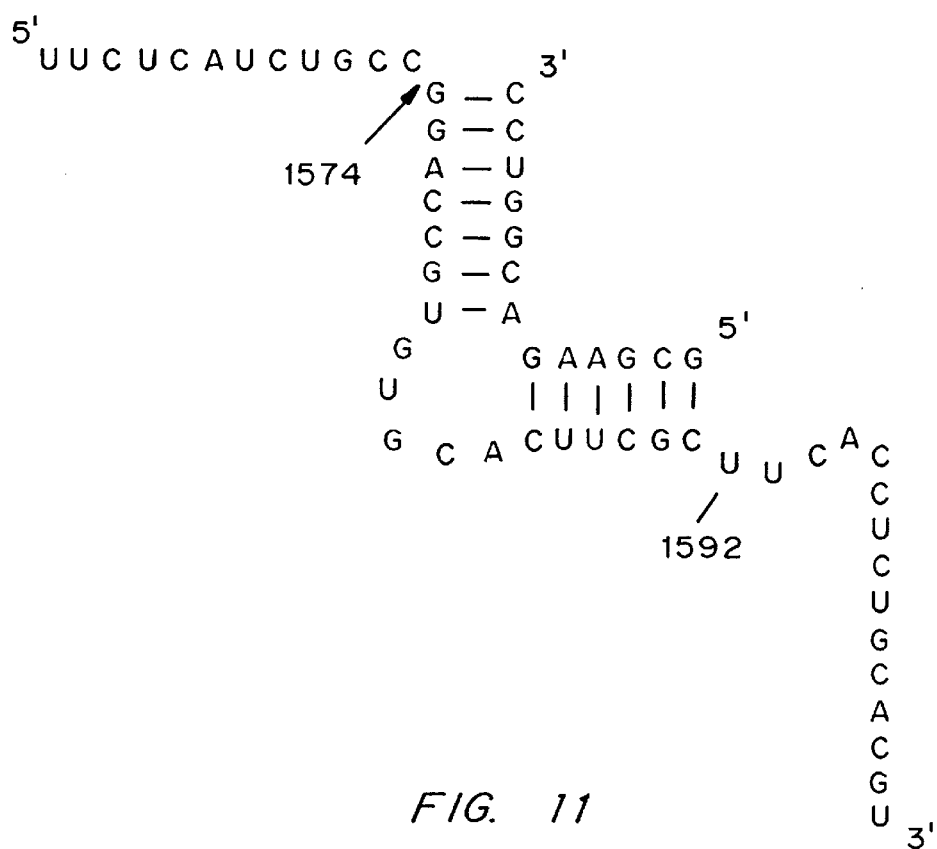
FIG. 11 is a diagram of the structure formed by hybridization of a SEGS (HBV H1) with the nucleotide sequence SEQ ID NO. 14 to a portion HBV RNA corresponding to nucleotides 1562–1606 of a 2.1 kb HBV RNA (nucleotides 4–48 of SEQ ID NO. 13). The SEGS and HBV RNA are aligned to show the base pairing which forms a structure similar to the A stem and T stem of tRNA. The RNAse P cleavage site is indicated with an arrow.

Design of a SEGS can be illustrated with an example. A portion of the nucleotide sequence of hepatitis B virus which contains a UNR motif is:CUGGAUGUGUCUGCGGCGU-UUUAUCAUCUUCCUCUUCAUCC UGCUGCUAU (SEQ ID NO. 7; UNR motif in bold). Choosing a T recognition arm length of five nucleotides, a bulge region length of nine nucleotides, an A recognition arm length of eight nucleotides, and a single spacer nucleotide in the turn region, the sequence for the SEGS is the complement of the five nucleotides adjacent to and 5' of the turn region, which includes a spacer nucleotide (U) 5' of the UNR motif, followed by the complement of the seven nucleotides starting at the fifteenth nucleotide 5' of the turn region. This SEGS (HBV B) will have a sequence of GAGGAAACGC-CGC (SEQ ID NO.6; T recognition arm in bold). The structure of the complex of SEGS HBV B and HBV RNA is shown in FIG. 7. Other examples also involving HBV are shown in FIGS. 8, 9, 10, and 11.

Figure 2:
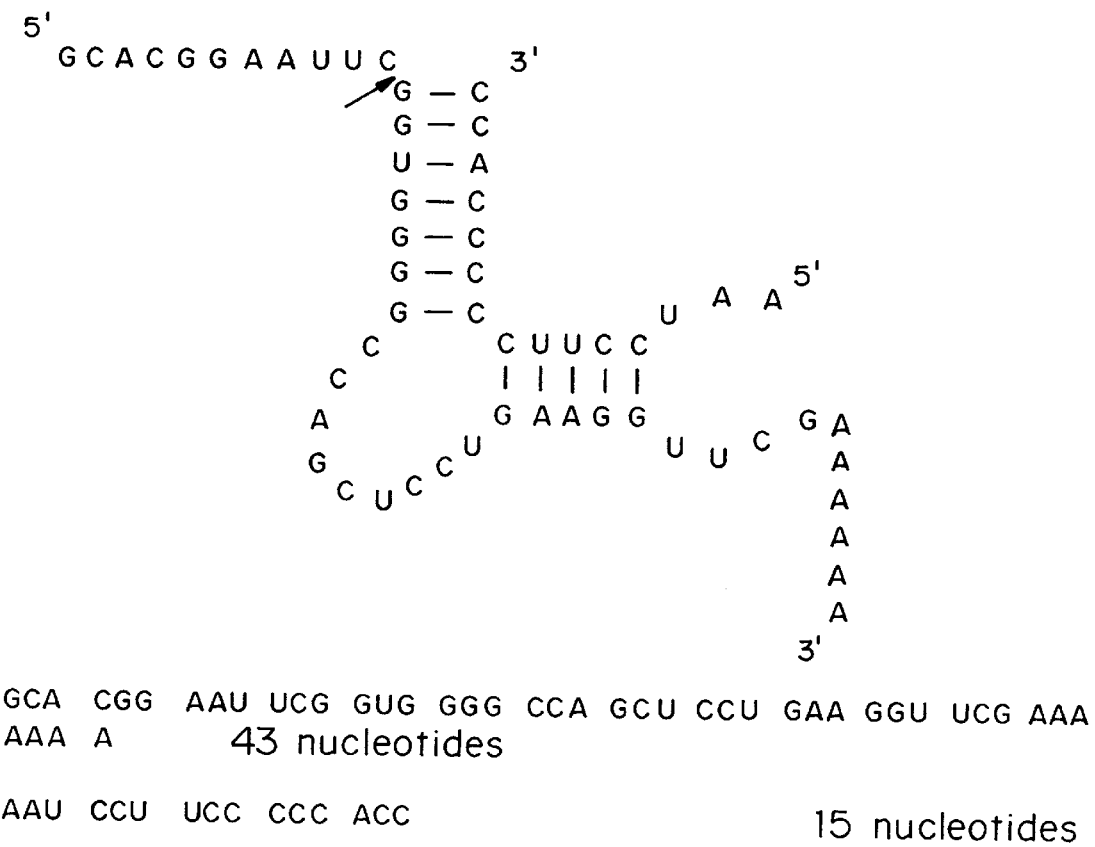
FIG. 2 is a diagram of the structure of a SEGS (EGS 3; SEQ ID NO. 1) and a short model target RNA (T 10) with the nucleotide sequence SEQ ID NO. 2. The two oligonucleotides are aligned to show the base pairing which forms a structure similar to the A stem and T stem of tRNA. This structure is recognized by eukaryotic RNAse P and promotes RNAse P-mediated cleavage of the target RNA. The RNAse P cleavage site is indicated with an arrow.

SEGS molecules may also contain additional nucleotide sequences at either or both of the 3' end of the A recognition arm and the 5' end of the T recognition arm. Such nucleotide regions are distinguished from the recognition sequence of the SEGS in that they are not complementary to the targeted sequence of the target RNA. Such sequences are not considered to be a part of the recognition sequence of the SEGS. An example of such an additional nucleotide sequence, at the 5' end of the T recognition arm, is shown in FIG. 2.

SEGS molecules can be readily screened for the ability to promote cleavage, by RNAse P, of target RNA using the assay described in Yuan et al., *Proc. Natl. Acad. Sci., USA,* 89:8006–8010 (1992) or the assay described below.

A SEGS and the catalytic RNA subunit of an RNAse P can be coupled to form a single oligonucleotide molecule possessing both the targeting function of the SEGS and cleavage function of RNAse P catalytic RNA. Such a combination, in a single oligonucleotide molecule, is referred to as an RNAse P internal guide sequence (RIGS). A RIGS can be used to cleave a target RNA molecule in the same manner as SEGS.

RIGSs can be formed by linking a guide sequence to an RNAse P catalytic sequence by any suitable means. For example, an SEGS and RNAse P catalytic RNA can be prepared as separate molecules which are then covalently coupled in vitro. Alternatively, a complete RIGS can be synthesized as a single molecule, either by chemical synthesis, or by in vitro or in vivo transcription of a DNA molecule encoding linked SEGS and RNAse P catalytic sequence. The linkage between the SEGS and RNAse P domains of an RIGS can have any form that allows the domains to cleave a target RNA. For example, the two domains could be joined by an oligonucleotide linker. Preferably, the linker will be composed of ordinary nucleotides joined by phosphodiester bonds. The SEGS and RNAse P catalytic sequence components can be joined in either order, with the RNAse P catalytic sequence linked to either the 3' end or 5' end of the SEGS component. Methods for the construction and use of RIGS are described in PCT application WO 95/24489 by Yale University.

The SEGS molecules can also be regulatable. A regulatable SEGS molecule is a SEGS sequence, as described above, linked to a ligand-binding sequence, placing the activity of the SEGS molecule under the control of that ligand and requiring the presence of the ligand for activation or inactivation. RNA molecules are constructed in which one portion is capable of binding a ligand and the other portion is a SEGS sequence. After the selection of molecules which bind the ligand, a second selection process occurs in which the ligand-binding molecules are assayed for their catalytic function in the presence and absence of the ligand or "co-drug." In this manner regulatable SEGS molecules are selected for use in cleaving a target RNA in the presence of a ligand, or in cleaving a target RNA in the absence of a ligand.

This method and regulatable SEGS molecules are useful in cleaving a target RNA molecule in a controlled fashion. It is particularly useful when the target RNA molecule is present in a cell where it is not desirable to kill the host cell by complete inactivation of these RNA molecules. The formation, selection and use of regulatable EGS molecules is fully described in PCT applications WO 94/13791 and WO 94/13833, which are hereby incorporated by reference. The same methods can be used to form select and use regulatable SEGS molecules.

Methods to produce or synthesize SEGS molecules, and DNA sequences encoding SEGS molecules having a known sequence, can be routinely synthesized using automated nucleic acid synthesis, for example, using the cyanoethyl phosphoramidite method on a DNA model 392 synthesizer by Applied Biosystems, Inc. (Foster City, Calif.) or a Pharmacia Oligo Pilot (Pharmacia, Piscataway, N.J.). Other methods for synthesizing nucleic acid molecules are also available (see, for example, Ikuta et al., *Ann. Rev. Biochem.* 53:323–356 (1984) (phosphotriester and phosphite-triester methods); Narang et al., *Methods Enzymol.* 65:610–620 (1980) (phosphotriester method). Alternatively, SEGS molecules can be synthesized by transcribing DNA templates, for example, with T7 RNA polymerase (Milligan et al., *Nucl Acids Res.* 15:8783 (1987)). SEGS molecules can also be synthesized in cells by placing a vector that encodes and expresses the SEGS in the cells.

B. Activity of SEGS Molecules

An in vitro cleavage assay which measures the percentage of substrate RNA remaining after incubation with various amounts of a SEGS, in the presence of a non-limiting amount of RNAse P, is used as an indicator of the potential activity of the SEGS/RNAse P complex. SEGS/RNAse P complexes that exhibit the highest in vitro activity are selected for further testing. The percentage of RNA remaining can be plotted as a function of the SEGS concentration. The catalytic efficiency of an SEGS/RNAse P can be expressed as $k_{cat}/K_m$ (where $k_{cat}$ is the rate constant of cleavage and $K_m$ is the Michaelis constant), the second order rate constant for the reaction of a free SEGS and substrate RNA molecule. Following the methods of Heidenreich and Eckstein (*J. Biol. Chem.*, 267:1904–1909 (1992)), $k_{cat}/K_m$ is determined using the formula $$-\ln F/t = (k_{cat}/K_m)[C]$$

where F is the fraction of substrate left, t is the reaction time, and [C] is the SEGS concentration.

Preferred SEGS constructs are those which bind to and promote the preferential RNAse P cleavage of the hepatitis substrate RNA. Preferred constructs can be selected using the ribozyme cleavage assay, as described in Example 1, and determining which constructs are the most efficient at mediating specific RNAse P cleavage of hepatitis substrate RNA sequence as determined by the value of $k_{cat}/K_m$, as described above.

Intracellular activity of SEGS can be tested using cells expressing the target RNA of interest. For example, SEGS molecules targeted to various regions of HBV RNA having the NUNR motif as described above can be tested in cells expressing HBV RNA. For this, SEGS can be tested in HepG2.2.15 cells, which constitutively express HBV RNA and fully assembled HBV particles (Sells et al., *Proc. Natl. Acad. Sci.* USA, 84:1005–1009 (1987)), for inhibition of viral replication. The assays can be preformed generally as described by Korba and Gerin (Antiviral Res. 19:55–70 (1992)). The SEGS molecules can be delivered to the cells as a complex with heme lipid particles, specifically 1,2-dioleoyloxy-3-(trimethylammonium)propane (DOTAP) and dioleoyl phosphatidyl ethanolamine (DOPE) conjugated with heme (referred to as DDH), for ten days and the DNA genome of HBV particles secreted into the media can be assayed using dot-blot assays.

Heme lipid particles can be prepared generally as follows. Heme (as Fe protoporphyrin IX chloride, hemin) is dissolved in ethanol containing 8.3 mM NaOH, and insoluble material is pelleted at 14 krpm for 10 minutes. To allow effective conjugation using carbodiimide, the pH of the heme solution is reduced by the addition of small volumes of HCl without precipitation of heme. In a typical reaction, 200 mg hemin is added to 10 ml ethanol containing 8.3 mM NaOH. HCl is added to the supernatant heme solution to bring the pH down to 1.7, the heme solution (containing approximately 1.6 mg heme), 760 μl (10 μmol) DOPE (10 mg/ml) and 500 μl DCC (10 mg/ml) is added and the conjugation is allowed to proceed overnight at room temperature in the dark. Ten micromoles DOTAP in chloroform are added to the heme-conjugated DOPE in a sterile glass test tube and the lipids are dried to a thin film, under vacuum in a vortex desiccator at 50° C. for 20 minutes. One milliliter sterile 150 mM NaCl is added to the lipid film and the emulsion was sonicated for 30 minutes in a Bransonic 1210 bath sonicator, operated at 47 kHz at 20° C., to give a turbid solution. The lipid particles are extruded through a polycarbonate membrane using a Lipex Extruder (Lipex Biomembranes, Vancouver, Canada).

The SEGS/lipid compositions are prepared by bringing solutions containing the SEGS molecules to 150 mM NaCl, and DDH lipid particles (in 150 mM NaCl) are added the SEGS solution to a final concentration of 0.2 mg/ml. After incubating for 15 minutes at room temperature, culture medium is added and the SEGS/lipid mixture is diluted to obtain SEGS compositions with the desired final concentration of SEGS. An equivalent volume of 150 mM NaCl is used as a control.

Confluent cultures of HepG2.2.15 cells are maintained on 96-well flat-bottomed culture plates. Duplicate plates are used for each SEGS treatment. A total of three cultures on each plate are treated with each of the diluted SEGS compositions. Cultures are treated with 10 consecutive daily doses of the SEGS compositions. Medium is changed daily with fresh SEGS compositions. The effect of these treatments is monitored by measuring extracellular HBV DNA levels.

The anti-viral activities of these SEGSs can be calculated as an $EC_{50}$. The $EC_{50}$ is the concentration of a compound at which there is a 50% reduction in the amount of HBV produced relative to cells treated with the control composition. For comparison, the anti-viral effect of 2'-3'-ddC, a known potent anti-HBV nucleoside analog, can be measured in the same assays.

A phenol red assay measuring the viability of cells that receive the SEGS can be used to determine if there is any toxicity (defined as greater than 50% depression of the dye uptake levels observed in untreated cells) associated with the administration of the SEGS.

II. Nuclease Resistant SEGS molecules

A. Types of Modifications

Although unmodified oligoribonucleotides can function as effective SEGS in a nuclease-free environment, the short half-life in serum and inside cells reduces their effectiveness as therapeutics. Chemical modifications can be made which greatly enhance the nuclease resistance of SEGS without compromising its biological function of promoting RNase P-mediated cleavage of target RNA. For example, one or more of the bases of an SEGS construct can be replaced by 2' methoxy ribonucleotides, phosphorothioate deoxyribonucleotides, or phosphorothioate ribonucleotides using available nucleic acid synthesis methods (see, for example, Offensperger et. al., *EMBO J.*, 12:1257–1262 (1993); WO 93/01286 by Rosenberg et al., (synthesis of sulfurthioate oligonucleotides); Agrawal et al., *Proc. Natl. Acad. Sci. USA,* 85:7079–7083 (1988); Sarin et al., *Proc. Natl. Acad. Sci. USA,* 85:7448–7794 (1989); Shaw et al., *Nucleic Acids Res,* 19:747–750 (1991) (synthesis of 3' exonuclease-resistant oligonucleotides containing 3' terminal phosphoroamidate modifications); incorporated herein by reference).

It is well documented in the current literature that degradation of oligonucleotide analogues is mainly attributable to 3'-exonucleases. Several studies have also demonstrated that various 3'-modifications can greatly decrease the nuclease susceptibility of these analogues. Thus, another method to reduce susceptibility to 3' exonucleases is introduction of a free amine to a 3' terminal hydroxyl group of the SEGS molecule (see, for example, Orson et al., *Nucl. Acids Res.,* 19:3435–3441 (1991)). Another useful 3' terminal modification is to couple a thymine nucleotide to the 3' end of an SEGS with a 3' to 3' linkage. Such a structure is referred to herein as 3'-3'-thymine nucleotide or T(3'—3'). Additional useful modifications include methylation of cytosine bases that may be present in the sequence, and covalent attachment of an intercalating agent, such as an acridine derivative, to a 5' terminal phosphate (for example, using a pentamethylene bridge), in order to reduce the susceptibility of a nucleic acid molecule to intracellular nucleases (see, for example, Maher et al., *Science,* 245:725–730 (1989); Grigoriev et al., *J. Biol. Chem.,* 267:3389–3395 (1992)).

Another class of chemical modifications expected to be useful is modification of the 2' OH group of a nucleotide's ribose moiety, which has been shown to be critical for the activity of the various intracellular and extracellular nucleases. Typical 2' modifications are the synthesis of 2'-O-Methyl oligonucleotides (Paolella et al., *EMBO J.,* 11:1913–1919, 1992) and 2'- fluoro and 2'-amino- oligonucleotides (Pieken, et al., *Science,* 253:314–317 (1991); Heidenreich and Eckstain, *J. Biol. Chem,* 267:1904–1909 (1992)). SEGS molecules can also contain deoxyribonucleotides. Such substitutions improve nuclease resistance by eliminating the critical 2' OH group.

WO 95/23225 by Ribozyme Pharmaceuticals, Inc. describes chemical modifications for increasing the stability of ribozymes, such as the introduction of an alkyl group at the 5' carbon of a nucleoside or nucleotide sugar. Such modifications can also be used in SEGS molecules. An alkyl group refers to a saturated aliphatic hydrocarbon, including straight chain, branch chain, and cyclic alkyl groups. It is preferred that such alkyl groups have 1 to 12 carbons. WO 95/23225 also describes 2'-deoxy-2'-alkylnucleotides which may be present to enhance the stability of oligonucleotides. For example, an oligonucleotide having at the 2'-position on the sugar molecule an alkyl moiety present where the nucleotide is not essential for function will be more stable. WO 95/23225 also describes the use of 3' and/or 5' dihalophosphonate substituted nucleotides, for example, 3' and/or 5'-$CF_2$-phosphonate substituted nucleotides. Such nucleotides can be used in SEGS molecules to enhance their nuclease resistance.

The extent to which such modifications affect the efficiency with which a modified SEGS molecule promotes ribozyme-mediated cleavage of target RNA can readily be determined using the cleavage assay described above.

The stability of SEGS/target RNA hybrids can be increased by using modified nucleotides that result in oligonucleoitdes with stronger base pairing to the target RNA. For example, C-5 propynyl pyrimide nucleotides increase hydrogen bonding between nucleic acids (Froehler et al., *Tetrahedron Letters* 33:5307–5310 (1992)).

B. Chimeric SEGS Molecules

The above modifications can be used throughout a SEGS molecule, in limited regions of a SEGS molecule and/or in combinations to result in chimeras of modified SEGS molecules. It is expected that all of the nucleotides in a SEGS can be chemically modified without significantly reducing its ability to promote RNAse P-mediated cleavage of a target RNA. For example, it has been discovered that 2'-O-methyl modified nucleotides can be used throughout a SEGS without a significant loss of RNAse P targeting activity.

The extent to which modifications affect the efficiency with which the modified SEGS molecule promotes RNAse P-mediated cleavage of a target RNA can readily be determined using the cleavage assay described above. Chemically modified SEGS molecules can be classified according to the level of ribozyme cleavage activity promoted by the modified SEGS when compared with the ribozyme cleavage activity promoted by an unmodified SEGS, that is, an SEGS molecule having the same nucleotide sequence as the modified SEGS but which is comprised of unmodified ribonucleotides, unmodified phosphodiester linkages, and unmodified 3' and 5' ends. This comparison provides the relative ribozyme cleavage activity promoted by the modified SEGS molecule, which is preferably expressed as a percentage of the ribozyme cleavage activity promoted by the unmodified SEGS molecule. Modified SEGS molecules can be divided into classes based on these activity levels. In this way, modified SEGS molecules can be divided, for example, into four classes: (1) modified SEGS molecules promoting greater than 70% of the ribozyme cleavage activity promoted by an unmodified SEGS, (2) modified SEGS molecules promoting from 50% to 70% of the ribozyme cleavage activity promoted by an unmodified SEGS, (3) modified SEGS molecules promoting from 25% to 50% of the ribozyme cleavage activity promoted by an unmodified SEGS, and (4) modified SEGS molecules promoting less than 25% of the ribozyme cleavage activity promoted by an unmodified SEGS. Preferred modified SEGS molecules promote at least 25 % of the ribozyme cleavage activity promoted by an unmodified SEGS. More preferred SEGS molecules promote at least 50% of the ribozyme cleavage activity promoted by an unmodified SEGS. The most preferred SEGS molecules promote at least 70% of the ribozyme cleavage activity promoted by an unmodified SEGS.

III. Cloning and Expression Vectors

Preferred vectors for introducing SEGS molecules into mammalian cells include viral vectors, such as the retroviruses, which introduce DNA which encodes an SEGS molecule directly into the nucleus where the DNA is then transcribed to produce the encoded SEGS molecule.

Examples of methods for using retroviral vectors for gene therapy are described in U.S. Pat. Nos. 4,868,116 and 4,980,286; PCT applications WO 90/02806 and WO 89/07136; and Mulligan, *Science* 260:926–932 (1993); the teachings of which are incorporated herein by reference.

Defective retroviral vectors, which incorporate their own RNA sequence in the form of DNA into the host chromosome, can be engineered to incorporate an SEGS into the cells of a host, where copies of the SEGS will be made and released into the cytoplasm or are retained in the nucleus to interact with the target nucleotide sequences of the hepatitis RNA.

Bone marrow stem cells and hematopoietic cells are relatively easily removed and replaced from humans, and provide a self-regenerating population of cells for the propagation of transferred genes. Such cells can be transfected in vitro or in vivo with retrovirus-based vectors encoding SEGS molecules. When in vitro transfection of stem cells is performed, once the transfected cells begin producing the particular SEGS molecules, the cells can be added back to the patient to establish entire clonal populations of cells that are expressing SEGS and are therefore resistant to viral infection, transformation, and other disorders.

As an example, a vector used to clone and express DNA sequences encoding constructs might include:

1. A cloning site in which to insert a DNA sequence encoding an SEGS molecule to be expressed.
2. A mammalian origin of replication (optional) which allows episomal (non-integrative) replication, such as the origin of replication derived from the Epstein-Barr virus.
3. An origin of replication functional in bacterial cells for producing required quantities of the DNA encoding the SEGS constructs, such as the origin of replication derived from the pBR322 plasmid.
4. A promoter, such as one derived from Rous sarcoma virus (RSV), cytomegalovirus (CMV), or the promoter of the mammalian U6 gene (an RNA polymerase III promoter) which directs transcription in mammalian cells of the inserted DNA sequence encoding the SEGS construct to be expressed.
5. A mammalian selection marker (optional), such as neomycin or hygromycin resistance, which permits selection of mammalian cells that are transfected with the construct.
6. A bacterial antibiotic resistance marker, such as neomycin or ampicillin resistance, which permits the selection of bacterial cells that are transformed with the plasmid vector.

A preferred vector for delivering and expressing SEGS molecules in vivo uses an RNA polymerase III (pol III) promoter for expression. Such promoters can produce transcripts constitutively without cell type specific expression. Pol III promoters also generate transcripts that can be engineered to remain in the nucleus of the cell, the location of many target RNA molecules. It is preferred that a complete pol III transcription unit be used, including a pol III promoter, capping signal, and termination sequence. Pol III promoters, and other pol III transcription signals, are present in tRNA genes, 5S RNA genes, small nuclear RNA genes, and small cytoplasmic RNA genes. Preferred pol III promoters for use in SEGS expression vectors are the human small nuclear U6 gene promoter and tRNA gene promoters. The use of U6 gene transcription signals to produce short RNA molecules in vivo is described by Noonberg et al., *Nucleic Acids Res.* 22:2830–2836 (1995), and the use of tRNA transcription signals is described by Thompson et al., *Nucleic Acids Res.*, 23:2259–2268 (1995), both hereby incorporated by reference.

Many pol III promoters are internal, that is, they are within the transcription unit. Thus, these pol III transcripts include promoter sequences. To be useful for expression of SEGS molecules, these promoter sequences should not interfere with the structure or function of the SEGS. Since SEGS molecules are derived from tRNA molecules, tRNA gene promoter sequences can be easily incorporated into SEGS molecules. The internal promoter of tRNA genes occurs in two parts, an A box and a B box. In tRNA molecules, A box sequences are generally present in the D loop and half of the D stem of tRNA molecules, and B box sequences are generally present in the T loop and the proximal nucleotides in the T stem. SEGS molecules lack most of these structures. However, both the B box and A box sequences can be appended to the 5' end of the SEGS, after the T recognition arm, such that the proper spacing between the A box and B box is maintained.

The U6 gene promoter is not internal (Kunkel and Pederson, *Nucleic Acids Res.* 18:7371–7379 (1989); Kunkel et al., *Proc. Natl. Acad. Sci.* USA 83:8575–8579 (1987); Reddy et al., *J. Biol. Chem.* 262:75–81 (1987)). Suitable pol III promoter systems useful for expression of SEGS molecules are described by Hall et al., *Cell* 29:3–5 (1982), Nielsen et al., *Nucleic Acids Res.* 21:3631–3636 (1993), Fowlkes and Shenk, *Cell* 22:405–413 (1980), Gupta and Reddy, *Nucleic Acids Res.* 19:2073–2075 (1990), Kickoefer et al., *J. Biol. Chem.* 268:7868–7873 (1993), and Romero and Blackburn, *Cell* 67:343–353 (1991). The use of pol III promoters for expression of ribozymes is also described in WO 95/23225 by Ribozyme Pharmaceuticals, Inc.

IV. Therapy

A. Pharmaceutical Compositions

SEGS molecules can be used directly in combination with a pharmaceutically acceptable carrier to form a pharmaceutical composition suited for treating a patient. Alternatively, an SEGS can be delivered via a vector containing a sequence which encodes and expresses the SEGS molecule specific for a particular RNA.

Direct delivery involves the insertion of pre-synthesized SEGS molecules into the target cells, usually with the help of lipid complexes (liposomes) to facilitate the crossing of the cell membrane and other molecules, such as antibodies or other small ligands such as heme or another porphyrin or phthalocyanin, to maximize targeting. Porphyrins complex with oligonucleotides, protecting as well as enhancing delivery to cells such as hepatocytes. Because of the sensitivity of RNA to degradation, in many instances, directly delivered SEGS molecules may be chemically modified, making them nuclease-resistant, as described above. This delivery methodology allows a more precise monitoring of the therapeutic dose.

Vector-mediated delivery involves the infection of the target cells with a self-replicating or a non-replicating system, such as a modified viral vector or a plasmid, which produces a large amount of the SEGS encoded in a sequence carried on the vector. Targeting of the cells and the mechanism of entry may be provided by the virus, or, if a plasmid is being used, methods similar to the ones described for direct delivery of SEGS molecules can be used. Vector-mediated delivery produces a sustained amount of SEGS molecules. It is substantially cheaper and requires less frequent administration than a direct delivery such as intravenous injection of the SEGS molecules.

The direct delivery method can be used during the acute critical stages of infection. Preferably, intravenous or subcutaneous injection is used to deliver SEGS molecules directly. It is essential that an effective amount of oligonucleotides be delivered in a form which minimizes degradation of the oligonucleotide before it reaches the intended target site.

Most preferably, the pharmaceutical carrier specifically delivers the SEGS to affected cells. For example, hepatitis B virus affects liver cells, and therefore, a preferred pharmaceutical carrier delivers anti-hepatitis SEGS molecules to liver cells.

HBV, a member of a group of small DNA-containing viruses that cause persistent non-cytopathic infections of the liver, is an infectious agent of humans that is found worldwide and which is perpetuated among humans in a large reservoir of chronic carriers. It is estimated that about 6–7% of the earth's population is infected (300 million carriers). The prevalence of the infection is not uniform throughout the world. There is a geographic gradient in distribution of HBV. It is lowest in North America and Western Europe, where the virus can be detected in 0.1 to 0.5% of the population, and highest in Southeast Asia and sub-Saharan Africa, where the frequency of infection may vary from 5 to 20% of the population. This skewed distribution parallels that of hepatocellular carcinoma and provides strong epidemiologic evidence for an association between chronic HBV infection and this type of malignancy.

Hepatitis B is of great medical importance because it is probably the most common cause of chronic liver disease, including hepatocellular carcinoma in humans. Infected hepatocytes continually secrete viral particles that accumulate to high levels in the blood. These particles are of two types: (i) noninfectious particles consisting of excess viral coat protein (HBsAg) and containing no nucleic acid (in concentrations of up to $10^{13}$ particles/ml blood), and (ii) infectious, DNA-containing particles (Dane particles) consisting of a 27 nm nucleocapsid core (HBcAg) around which is assembled an envelope containing the major viral coat protein, carbohydrate, and lipid, present in lower concentrations ($10^9$ particles/ml blood). The human hepatitis B virus is a member of the Hepadna Viridae family, with close relatives including woodchuck hepatitis virus (WHV), duck hepatitis virus (DHV), and ground squirrel hepatitis virus (GHV) (Robinson (1990)). Like retroviruses, the hepadnavirus utilizes reverse transcription of its 3.2 kb DNA genome (Pugh (1990)). The genome of hepatitis B virus is circular and partially single-stranded, containing an incomplete plus strand. The incomplete plus strand is complexed with a DNA polymerase in the virion which has been shown to elongate the plus strand using the complete minus strand as the template. These morphological and structural features distinguish hepatitis B viruses from all known classes of DNA-containing viruses.

The replication cycle of hepatitis B viruses is also strikingly different from other DNA-containing viruses and suggests a close relationship with the RNA-containing retroviruses. The principal unusual feature is the use of an RNA copy of the genome as an intermediate in the replication of the DNA genome. Infecting DNA genomes are converted to a double-stranded form which serves as a template for transcription of RNA. Multiple RNA transcripts are synthesized from each infecting genome, which either have messenger function or DNA replicative function. The latter, termed "pre-genomes," are precursors of the progeny DNA genomes because they are assembled into nucleocapsid cores and reverse-transcribed into DNA before coating and export from the cell. Thus each mature virion contains a DNA copy of the RNA pre-genome and a DNA polymerase.

The first DNA to be synthesized is of minus strand polarity and is initiated at a unique site on the viral genetic map. Very small nascent DNA minus strands (less than 30 nucleotides) are covalently linked to a protein, and are likely to act as primer for minus strand DNA synthesis. Growth of the minus strand DNA is accompanied by a coordinate degradation of the pre-genome so that the product is a full-length single-stranded DNA, rather than an RNA:DNA hybrid. Plus strand DNA synthesis has been observed only after completion of the minus strand, and initiates at a unique site close to the 5' end of the minus strand. Complete elongation of the plus strand is not a requirement for coating and export of the nucleocapsid cores, thus most extracellular virions contain incomplete plus strands and a large single-stranded gap in their genomes. Because the hepatitis virus genome is autonomous and does not utilize a DNA-to-DNA pathway for its replication, continuous intracellular replication of its genome is essential for the maintenance of the virus.

The hepatitis B virus surface antigens (HBsAgs), which make up the viral envelope, are polypeptides encoded by the pre-S1, pre-S2 and S genes of the virus. The major protein is the 226 amino acid S gene product derived from a 2.1 kb subgenomic message. As demonstrated by the following example, SEGS have been designed which target HBV nucleic acid, and inhibit replication, leading to decreased viral loads.

B. Delivery of SEGS Molecules

Two methods of delivery may be employed, (1) delivery of synthetic SEGS molecules, or (2) delivery of a vector expressing SEGS molecules in a transient fashion. The method of choice will be determined in preclinical studies, using standard methodology, and it is possible that they may be used in combination. Both of them can be efficiently delivered, for example, by using cationic liposome preparations.

A variety of non-vector methods are available for delivering SEGS molecules to cells. For example, in general, the SEGS molecules, or DNA sequences encoding the SEGS molecules, can be incorporated within or on microparticles. As used herein, microparticles include liposomes, virosomes, microspheres and microcapsules formed of synthetic and/or natural polymers. Methods for making microcapsules and microspheres are known to those skilled in the art and include solvent evaporation, solvent casting, spray drying and solvent extension. Examples of useful polymers which can be incorporated into various microparticles include polysaccharides, polyanhydrides, polyorthoesters, polyhydroxides and proteins and peptides.

Liposomes can be produced by standard methods such as those reported by Kim et al., *Biochim. Biophys. Acta,* 728:339–348 (1983); Liu et al., *Biochim. Biophys. Acta,* 1104:95–101 (1992); and Lee et al., *Biochim. Biophys. Acta.,* 1103:185–197 (1992); Wang et al., *Biochem.,* 28:9508–9514 (1989)), incorporated herein by reference. SEGS molecules or DNA encoding such molecules, can be encapsulated within liposomes when the molecules are present during the preparation of the microparticles. Briefly, the lipids of choice, dissolved in an organic solvent, are mixed and dried onto the bottom of a glass tube under vacuum. The lipid film is rehydrated using an aqueous buffered solution of the SEGS molecules, DNA encoding SEGS molecules to be encapsulated, and the resulting hydrated lipid vesicles or liposomes encapsulating the material can then be washed by centrifugation and can be filtered and stored at 4° C. This method has been used to deliver nucleic acid molecules to the nucleus and cytoplasm of cells of the MOLT-3 leukemia cell line (Thierry and Dritschilo, *Nucl. Acids Res.,* 20:5691–5698 (1992)). Alternatively, SEGS molecules, or DNA encoding such molecules, can be incorporated within microparticles, or bound to the outside of the microparticles, either ionically or covalently.

Cationic liposomes or microcapsules are microparticles that are particularly useful for delivering negatively charged compounds such as nucleic acid-based compounds, which can bind ionically to the positively charged outer surface of these liposomes. Various cationic liposomes have previously been shown to be very effective at delivering nucleic acids or nucleic acid-protein complexes to cells both in vitro and in vivo, as reported by Felgner et al., *Proc. Natl. Acad. Sci. USA*, 84:7413–7417 (1987); Feigner, *Advanced Drug Delivery Reviews*, 5:163–187 (1990); Clarenc et al., *Anti-Cancer Drug Design*, 8:81–94 (1993), incorporated herein by reference. Cationic liposomes or microcapsules can be prepared using mixtures including one or more lipids containing a cationic side group in a sufficient quantity such that the liposomes or microcapsules formed from the mixture possess a net positive charge which will ionically bind negatively charged compounds. Examples of positively charged lipids that may be used to produce cationic liposomes include the aminolipid dioleoyl phosphatidyl ethanolamine (PE), which possesses a positively charged primary amino head group; phosphatidylcholine (PC), which possess positively charged head groups that are not primary amines; and N[1-(2,3-dioleyloxy)propyl]-N,N,N-triethylammonium ("DOTMA," see Felgner et al., *Proc. Natl. Acad. Sci USA*, 84:7413–7417 (1987); Felgner et al., *Nature*, 337:387–388 (1989); Feigner, *Advanced Drug Delivery Reviews*, 5:163–187 (1990)).

A preferred form of microparticle for delivery of SEGS molecules are heme-bearing microparticles. In these microparticles, heme is intercalated into or covalently conjugated to the outer surface of the microparticles. Heme-bearing microparticles offer an advantage in that since they are preferentially bound and taken up by cells that express the heme receptor, such as hepatocytes, the amount of drug or other compound required for an effective dose is significantly reduced. Such targeted delivery may also reduce systemic side effects that can arise from using relatively high drug concentrations in non-targeted delivery methods. Preferred lipids for forming heme-bearing microparticles are 1,2-dioleoyloxy-3-(trimethylammonium)propane (DOTAP) and dioleoyl phosphatidyl ethanolamine (DOPE). The production and use of heme-bearing microparticles are described in PCT application WO 95/27480 by Innovir.

Nucleic acid can also be encapsulated by or coated on cationic liposomes which can be injected intravenously into a mammal. This system has been used to introduce DNA into the cells of multiple tissues of adult mice, including endothelium and bone marrow, where hematopoietic cells reside (see, for example, Zhu et al., *Science*, 261:209–211 (1993)).

Liposomes containing either SEGS molecules or DNA encoding these molecules, can be administered systemically, for example, by intravenous or intraperitoneal administration, in an amount effective for delivery of the anti-hepatitis SEGS molecules to targeted cells. Other possible routes include trans-dermal or oral, when used in conjunction with appropriate microparticles. Generally, the total amount of the liposome-associated nucleic acid administered to an individual will be less than the amount of the unassociated nucleic acid that must be administered for the same desired or intended effect.

As described in the application co-filed with this application entitled "Delivery of Nucleic Acids using Porphyrins" by Garry B. Takle and Shaji B. George, another delivery system is described wherein the SEGS is complexed ionically to a porphyrin, which protects as well as targets the SEGS to hepatocytes following injection.

Compositions including various polymers such as the polylactic acid and polyglycolic acid copolymers, polyethylene, and polyorthoesters and the anti-hepatitis SEGS molecules, or DNA encoding such molecules, can be delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, Johnson and Lloyd-Jones, eds., *Drug Delivery Systems* (Chichester, England: Ellis Horwood Ltd., 1987), which can effect a sustained release of the therapeutic anti-hepatitis SEGS compositions to the immediate area of the implant.

SEGS can also be applied topically, for example for the treatment of psoriasis or opthalmic disorders, in a suitable topical carrier such as an ointment, salve, buffered saline solution, or other pharmaceutically acceptable topical or ophthalmic carrier.

The following examples are presented for illustrative purposes and additional guidance.

EXAMPLES

Example 1

Oligonucleotide Synthesis, Plasmids and Transcription Reactions for Construction and Analysis of SEGS Molecules Oligonucleotides: Oligoribonucleotides (RNA) were prepared according to the method of Ogilvie et al., *Proc. Natl. Acad. Sci. U.S.A.*, 85:5764–5768 (1988), employing 5'-dimethoxytrityl-2'-methylsilyl-ribonucleoside 3'-CE-phosphoramidites (Biosearch, Mass., or ChemGenes Corp., Mass.). 2'-O-methyl oligoribonucleotides (2'-O-methyl RNA) were synthesized using RNA synthesis protocols of, and amidites were purchased from, either Biosearch or Glen Research. Syntheses were performed on a Millipore 8909 Experdite DNA/RNA synthesizer. Controlled pore glass (CPG) were used as the solid support matrix. The coupling time was about 13 minutes. For the syntheses of analogues containing phosphorothioate linkages, oxidation was replaced by sulfurization which was carried out using Beaucage reagent for 10 to 15 minutes. The average coupling yield, as assayed by trityl measurement, was 96 to 98%.

Cleavage from the support, base and phosphate deprotection, and removal of the 2'-O-TBDMS group were performed as described by Scaringe et al., *Nucleic Acids Research*, 18:5433–5441 (1990). The crude oligonucleotides in TBAF solution were desalted on a Sephadex G-25 column prior to standard electrophoretic purification using 15–20% polyacrylamide/7M urea gels. Product bands were visualized by UV-shadowing, cut out, and eluted from the gel matrix. The eluted oligomers were finally desalted on a $C_{18}$ Sep-Pak cartridge and quantified by $OD_{260}$ measurement. Homogeneity of the purified analogues was checked by 5'-end labeling or analytical HPLC. They can be further characterized by base composition analysis, as described by Seela and Kaiser, *Nucleic Acids Res.*, 15:3113–3129 (1987), and the content of thioate linkages quantitated by $^{31}P$-NMR. Terminal modifications of the 3'-end were made by starting the synthesis from a modified CPG support containing an amino group.

RNAse P Cleavage Assays: Cleavage reactions were carried out generally according to the procedure described by Yuan et al., *Proc. Natl. Acad. Sci., USA*, 89:8006–8010, (1992), which is hereby incorporated by reference. Briefly, short substrate reactions were made up to a total volume of 31 $\mu$ in 50 mM Tris-HCl pH 7.4, 10 mM $MgCl_2$, 25 mM KCl, 0.1 mM EDTA, with an SEGS concentration of 200–400 nM, and a target molecule concentration of 50 nM or less. The reactions were incubated at 37° C. for 1 hour. After incubation, the reaction solution was mixed with loading buffer (98% formamide, 10 mM EDTA, 0.025% bromophenol blue). The cleaved substrate was separated from the uncleaved by electrophoresis on a 15% acrylamide gel containing 7M urea. The bands were quantified on a Molecular Dynamics Phosphorimager.

The bands corresponding to the RNA substrate and the resulting two cleavage products were counted from the dried gel using a Betascope gel analyzer (Betagen).

RNAse P was purified by DEAE Sepharose chromatography and glycerol density gradient centrifugation essentially as described by Bartkiewicz et al., *Genes Dev.* 3:488–499 (1989), which is hereby incorporated by reference.

To test cleavage with a longer target RNA molecules generated by transcription, different reaction conditions were used. Reactions in a total volume of 10 μl contained 40 mM Tris-HCl (pH 7.4), 10 mM MgCl$_2$, 1 mM spermidine 10 mM dithiothreitol, 0.05 μg/μl nuclease-free bovine serum albumin, 0.01% (v/v) Triton-X100, 0.8 Units/μl RNASIN, 0.2 mM ATP, 0.2 mM GTP, 0.2 mM UTP, 0.2 mM CTP, 0.1 μCi/μl [α$^{32}$P] CTP, 2 mM m$^7$G(5')pppG, 0.06 μg/μl yeast RNA, 25 mM KCl, 3 Units T7 RNA polymerase, 250 nM SEGS, 1 μl of human RNAse P and 3 ng/μl linearized plasmid. Reactions were initiated by the addition of linearized plasmid and incubated for 30 minutes at 37° C. Reactions were terminated by the addition of 10 μl of 80% formamide, 10 mM EDTA, 0.1% bromphenol blue. After heating for 2 minutes at 90° C., samples were electrophoresed for 2 hours at 48 watts on a 5% denaturing polyacrylamide gel. After vacuum drying for 1 hour at 60° C., the gel was analyzed by phosphoimaging.

The percentage of RNA substrate remaining in either assay was plotted as function of the SEGS concentration and the catalytic efficiency expressed as $k_{cat}/K_m$ (where $k_{cat}$ is the rate constant of cleavage and $K_m$ is the Michaelis constant), the second order rate constant for the reaction of free SEGS and substrate. Following the methods of Heidenreich and Eckstein (J. *Biol. Chem.*, 267:1904–1909 (1992), the efficiency of the cleavage reaction, $k_{cat}/K_m$), was determined using the formula $$-\ln F/t = (k_{cat}/K_m)[C]$$

where F is the fraction of RNA substrate left, t is the reaction time, and [C] is the SEGS concentration.

Fetal Calf Serum Stability Assay: The nuclease resistance of modified SEGS molecules can be tested in a Fetal Calf Serum (FCS) Assay. It was reported by Shaw et al., *Nucleic Acids Res.* 19:747–750 (1991), that 10% FCS, when heated inactivated, mimics rather closely the human serum. The assay conditions are very similar to that previously described by Hoke et al., *Nucleic Acids Res.* 19:5743–5748 (1991) . Briefly, an SEGS analog to be tested is 5'-end labeled with T4 polynucleotide kinase and [γ-$^{35}$S] ATP (this procedure can generate radiolabeled oligonucleotides which are resistant against dephosphorylation). The labeled SEGS is then purified by phenol/chloroform extraction, followed by a Sephadex G-25 spin-column filtration. The purified SEGS is mixed with cold SEGS and 10% heat-inactivated fetal calf serum (FCS) so that the final concentration of SEGS is about 5 μM. SEGS analogues are treated over a period of 24 hours. Aliquots are withdrawn from the reaction mixture at different time points, mixed with 2X loading dye, heat inactivated at 90° C. for 3 min, then stored at –20° C. The results are analyzed on 12% polyacrylamide/7M urea gels.

Example 2

Activity of SEGS molecules in promoting RNAse P cleavage

SEGS Constructs Modeled on tRNA: The activities of SEGS and model target RNA molecules having various sequences and structures modeled on tRNA sequences were tested. Activities were measured in terms of the percent of substrate cleaved in one hour, as described in Example 1. A comparison was made between a SEGS with T loop sequences appended onto the T recognition arm (SEGS 3; SEQ ID NO. 1; see FIG. 2) and a SEGS without any appended sequence (SEGS 7; nucleotides 4-15 of SEQ ID NO. 1; see FIG. 5). This was done, in part, to test whether the T loop sequences other than the UNR motif affect promotion of RNAse P-mediated cleavage in a SEGS. The SEGS molecules used are shown in FIG. 5. The 15 nucleotide SEGS has appended T loop sequence and the 12 nucleotide SEGS does not. The activities of these two SEGS in promoting cleavage of a model substrate (T 10, also shown in FIGS. 2 and 5) are listed in rows one and two in Table 1. It is clear that the appended nucleotides have no significant effect on cleavage activity. The first column in Table 1 shows the sequence of the turn region and, in the case of these examples, a short tail sequence made up of six adenine nucleotides. This is indicated by (A).

TABLE 1

Cleavage Activity of Different Turn Region Sequences

| Turn Region Sequence | % Cleavage | SEGS + Target | Comments |
|---|---|---|---|
| U U C G (A) | 96 | EGS 7 + T 10 | 12 nt SEGS |
| U U C G (A) | 94 | EGS 3 + T 10 | 15 nt SEGS |
| U U C (A) | 96 | EGS 3 + T 11 | 15 nt SEGS |
| U C C G (A) | 13 | EGS 3 + T 12 | 15 nt SEGS |
| U C G (A) | 62 | EGS 3 + T 13 | 15 nt SEGS |
| U U U G (A) | 10 | EGS 3 + T 14 | 15 nt SEGS |
| C U C G (A) | 53 | EGS 3 + T 15 | 15 nt SEGS |
| U U C G (A) | 45 | EGS 6 + T 16 | G-C pair adjacent to cleavage site changed to C-G pair |
| U U C G (A) | 49 | EGS 7m + T 10 | all 2'0-methyl |
| U U C (A) | 60 | EGS 7m + T 11 | all 2'0 methyl |

Effect of Sequence in the Turn Region and at the Cleavage Site on SEGS Activity: Various model target RNA molecules were designed differing only in the sequence of the turn region. The substrates have the same nucleotide sequence as target RNA T 10 (SEQ ID NO. 2) except for the turn region. Activity was assayed using EGS 3 (SEQ ID NO. 1). The assays were performed as described above with 50 nM target RNA, 400 nM SEGS, and 3 μl RNAse P. The activity of these SEGS are shown in rows two through seven in Table 1. All of the variants are actively cleaved to a significant extent. In these examples, particular sequences are less favorable than others, such as UCCG and UUUG. These results confirm that SEGS can be designed for target sequences having a wide range of sequences 3' of the second target region.

The nucleotide at the 3' end of the A recognition arm (which is involved in the base pair adjacent to the cleavage site) of SEGS EGS 3 was changed from a cytidine nucleotide to a guanine nucleotide. The target RNA sequence was correspondingly changed. The activity of the resulting SEGS (EGS 6) is shown in row eight of Table 1. This activity (45% cleavage), while lower than the SEGS with a cytidine nucleotide (row two in Table 1), is still significant. This indicates that while a cytidine nucleotide at the 3' end of the A recognition arm is preferable, it is not required. While the variant turn region and 3' end sequences affected the activity of the SEGS, all had measurable and useful activity.

Effect of Chemical Modifications on SEGS Activity: 2'-O-methyl-oligoribonucleotides have several favorable features as a logical choice to modify. The synthesis of these analogues is very similar to that of the DNA synthesis. They have a much better binding affinity to RNA target than DNA analogues and the resulting duplexes have a structure between that of a RNA-RNA duplex (A-form) and DNA-DNA duplex (B-form). In addition, they prove to be fairly resistant to degradation by either RNA- or DNA-specific nucleases. 2'-O-methyl-oligoribonucleotide SEGS were made modeled on EGS 7 (nucleotide 4-15 of SEQ ID NO. 1). The activities of this chemically modified SEGS with two substrates are shown in rows nine and ten in Table 1. These activities, while lower than activities obtained with unmodified SEGS (compare with rows one and three in Table 1), are still significant. This indicates that a SEGS can have all of its nucleotides chemically modified and still retain significant activity.

Effect of Length of Recognition Arms and Bulge Region on SEGS Activity: To gauge the effects of the length of the recognition arms and the bulge region, various SEGS and model target RNAs were constructed having different combinations of lengths for these regions. The substrates were modeled after target RNA T 10. The SEGS molecules were modeled after EGS 7. The assays were performed as described above with 33 nM target RNA, 333 nM SEGS, and 3 µl RNAse P. The length combinations tested, and the activity observed, are shown in Table 2. The starting lengths to which changes were made were a 7 base pair A stem, a 5 base pair T stem, and a 9 nucleotide bulge region. This combination has a high activity (see row one in Table 2).

TABLE 2

Cleavage Activity of Different Constructs

| Base Pairs in A Stem | Base Pairs in T Stem | Nucleotides in Bulge | % Cleavage | Construct |
|---|---|---|---|---|
| 7 | 5 | 9 | 92 | T 10 + EGS 7 |
| 8 | 5 | 9 | 91 | T 10 + EGS 9 |
| 9 | 5 | 9 | 36 | T 10 + EGS 10 |
| 10 | 5 | 9 | 10 | T 10 + EGS 11 |
| 7 | 6 | 9 | 93 | T 17 + EGS 8 |
| 7 | 7 | 9 | 10 | T 18 + EGS 5 |
| 8 | 6 | 9 | 23 | T 17 + EGS 12 |
| 7 | 5 | 7 | 95 | T 19 + EGS 7 |
| 7 | 5 | 11 | 92 | T 20 + EGS 7 |
| 7 | 5 | 13 | 95 | T 21 + EGS 7 |
| 7 | 5 | 15 | 92 | T 22 + EGS 7 |

The first group of rows in Table 2 (rows one to four) show results with A stem lengths of 7, 8, 9, and 10 base pairs. All are active, although the SEGS with 10 nucleotides in the A recognition arm is less active. This indicates that an A recognition arm of 7, 8, or 9 nucleotides is preferable. The second group of rows in Table 2 (rows five to seven) show results with T stem lengths of 6 and 7 base pairs. Row seven combines an 8 base pair A stem with a 6 base pair T stem. All are active, although the SEGS with 7 nucleotides in the T recognition arm is less active. This indicates that an T recognition arm of 5 or 6 nucleotides is preferable. The third group of rows in Table 2 (rows eight to eleven) show results with bulge region lengths of from 7 to 15 nucleotides. All of these constructs are highly active. This indicates that the length of the bulge region is not a significant determinant of SEGS activity. Overall, these results indicate that an A recognition arm of 7 nucleotides and a T recognition arm of 5 nucleotides are most preferred. While these changes affect the activity of the SEGS, most changes had little effect and all of the SEGS had measurable and useful activity.

Figure 12:
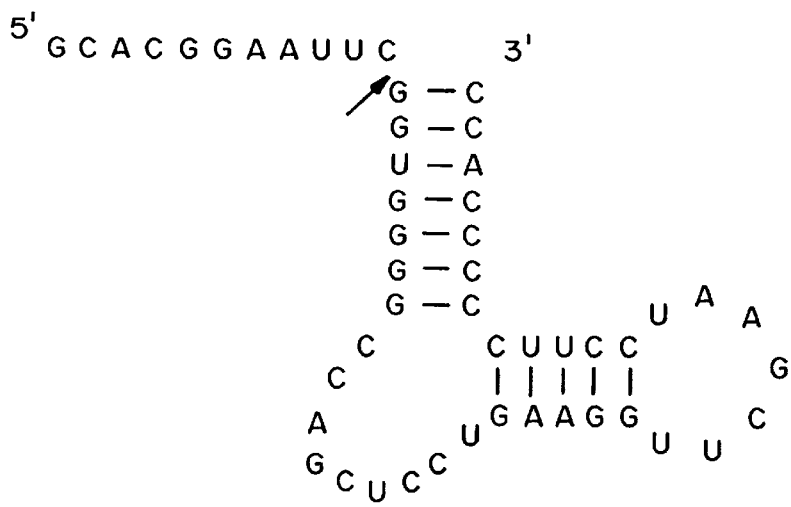
FIG. 12 is a diagram of the structure of a minimal RNAse P substrate which is similar to an SEGS/target RNA complex. The nucleotide sequence of the substrate is SEQ ID NO. 15. This structure is recognized and cleaved by eukaryotic RNAse P. The RNAse P cleavage site is indicated with an arrow. The sequences involved in the stems and in the T loop are the same as the sequences in the A stem and T stem and loop of tRNA$^{Tyr}$.
Figure 13:
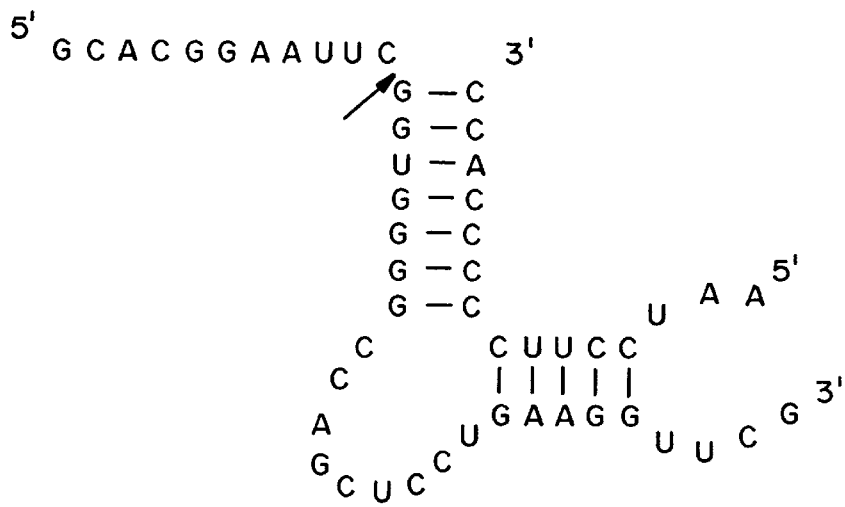
FIG. 13 is a diagram of the structure of a SEGS (EGS 3) with the nucleotide sequence SEQ ID NO. 1 and a short model target RNA (T 7) with the nucleotide sequence shown in nucleotides 1 to 36 of SEQ ID NO. 2. The two oligonucleotides are aligned to show the base pairing which forms a structure similar to the A stem and T stem of tRNA. This structure is recognized by eukaryotic RNAse P and promotes RNAse P-mediated cleavage of the target RNA. The RNAse P cleavage site is indicated with an arrow. The sequences involved in the stems and in the "broken" T loop are the same as the sequences in the A stem and T stem and loop of tRNA$^{Tyr}$.

Comparison of SEGS Activity and Activity of RNAse P substrates: The cleavage activities of minimal RNAse P substrates forming structures similar to SEGS/target RNA complexes were compared to the activity of SEGS molecules. RNAse P substrates are single nucleotide molecules containing both the RNAse P cleavage site and a guide sequence. Unlike SEGS/target RNA complexes, RNAse P substrate have an intact T loop. FIGS. 12 and 13 show a minimal RNAse P substrate and a SEGS/target RNA complex, respectively. Both are modeled on the sequence of $tRNA^{Tyr}$. In RNAse P activity assays as described in Example 1, the RNAse P substrate was 99% cleaved in one hour and the SEGS promoted cleavage of 95% of the target RNA.

Figure 3:
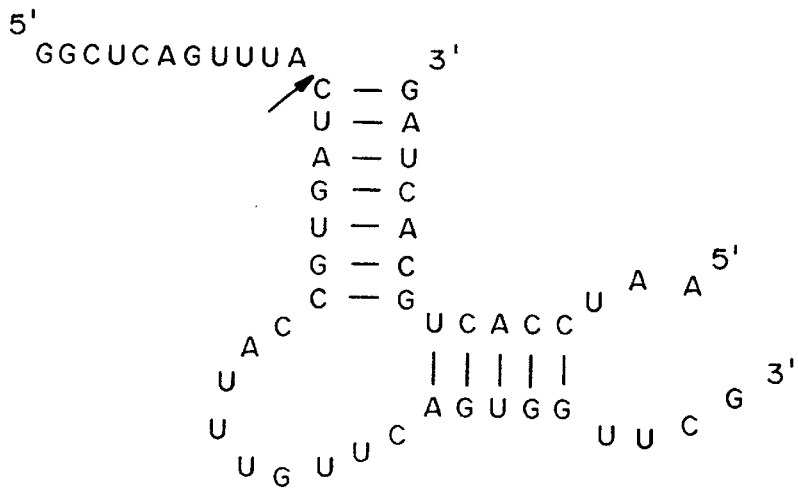
FIG. 3 is a diagram of the structure of a SEGS (EGS a) with the nucleotide sequence SEQ ID NO. 3 and a short model target RNA (T a) with the nucleotide sequence shown in nucleotides 1 to 36 of SEQ ID NO. 4. The two oligonucleotides are aligned to show the base pairing which forms a structure similar to the A stem and T stem of tRNA. This structure is recognized by eukaryotic RNAse P and promotes RNAse P-mediated cleavage of the target RNA. The RNAse P cleavage site is indicated with an arrow. Part of the model target RNA matches a portion of HBV sequence. The sequence involved in the "broken" T loop are the same as the sequences in the T loop of tRNA$^{Tyr}$.
Figure 6:
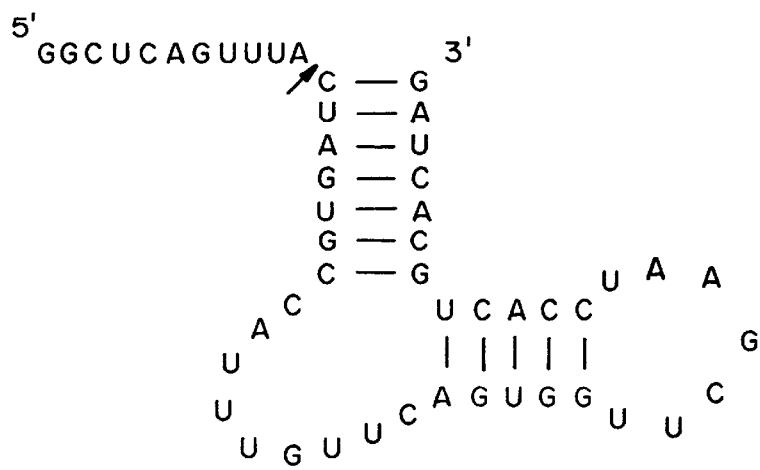
FIG. 6 is a diagram of the structure of a minimal RNAse P substrate which is similar to an SEGS/target RNA complex. The nucleotide sequence of the substrate is SEQ ID NO. 5. This structure is recognized and cleaved by eukaryotic RNAse P. The RNAse P cleavage site is indicated with an arrow. The sequence is model on a portion of HBV sequence.

RNAse P substrates and SEGS/target RNA pairs were also modeled after HBV sequences. FIGS. 3 and 6 show examples of such a SEGS/target RNA pair and an RNAse P substrate, respectively. In RNAse P activity assays as described in Example 1, the RNAse P substrate was 80% cleaved in one hour and the SEGS promoted cleavage of 65% of the target RNA. These results show that SEGS/target RNA complexes retain a significant fraction of the activity present in RNAse P substrates containing a T loop, even in the case of SEGS modeled after arbitrary sequences.

Example 3

Construction and Activity of SEGS Molecules Promoting RNAse P Cleavage of HBsAg RNA SEGS molecules were designed to promote cleavage by RNAse P in RNA encoding HBsAg. In the presence of target, the SEGS molecules formed a structure similar to the A stem and T stem of tRNA which elicited cleavage by RNAse P.

SEGS Constructs Targeted to HBsAg: SEGS sequences HBV B (SEQ ID NO. 6), HBV C (SEQ ID NO. 8), HBV F1 (SEQ ID NO. 10), HBV H (SEQ ID NO. 12), and HBV H1 (SEQ ID NO. 14) were designed to target regions of RNA encoding hepatitis B surface antigen (HBsAg). The regions were chosen as described earlier by identifying the location of UNR motifs in HBsAg-encoding RNA. As shown in FIG. 7, the sequence of one of the recognition arms (the A recognition arm; nucleotides 6–13 of SEQ ID NO. 6) of SEGS HBV B is complementary to eight nucleotides in the sequence encoding HBsAg (nucleotides 13–20 of SEQ ID No. 7; nucleotides 387–394 of the 2.1 kb HBV transcript). The sequence of the other recognition arm (the T recognition arm; nucleotides 1–5 of SEQ ID NO. 6) of SEGS HBV B is complementary to five nucleotides in the sequence encoding HBsAg (nucleotides 30–34 of SEQ ID No. 7; nucleotides 404–408 of the 2.1 kb HBV transcript). Thus, the target sequence contains two regions (the first and second target regions) complementary to the two recognition arms of the SEGS which are separated by 9 unpaired nucleotides (the bulge region).

2'-O-methyl-containing SEGS molecules: The SEGS molecules targeting HBV were prepared containing 2'-O-methyl nucleotides. These oligonucleotides were prepared in an automated oligonucleotide synthesizer as described earlier except that the nucleotide reagents contained a 2'-O-methyl group. The average coupling yield, as assayed by trityl measurements, was in the range of 96 to 98%. Upon completion of deprotection, fully deprotected oligonucleotides were purified by denaturing gel electrophoresis and their purity assessed by 5'-end labeling, analytical HPLC, base composition analysis and $^{31}$P-NMR.

Cleavage of Large Target RNA Promoted by SEGS: The SEGS specific for HBV RNA sequences were assayed using the RNAse P cleavage assays described in Example 1 to determine the efficiency of the cleavage reaction. For this, plasmid pAYW2.1, containing the sequence that encodes the 2.1 kb RNA of the AYW strain of HBV, was linearized by digestion with Not I, and then transcribed by T7 RNA polymerase in the presence of [$\alpha^{32}$P]CTP. Labeled transcripts were incubated for 30 minutes at 37° C. with RNAse P in the presence of various SEGS molecules. Reaction products were subjected to denaturing polyacrylamide gel electrophoresis, and analyzed by phosphoimaging. Each of the SEGS specific for HBV RNA described above produced a visible cleavage band on the gel image. This indicates that SEGS designed for arbitrary target sequences in large, natural target RNA molecules are functional.

Modifications and variations of the method of the present invention will be obvious to those skilled in the art from the foregoing detailed description. Such modifications and variations are intended to come within the scope of the appended claims.

We claim:

1. A Short External Guide Sequence oligonucleotide molecule comprising
a recognition sequence complementary to regions of a targeted sequence in a target RNA molecule, wherein the recognition sequence comprises an A recognition arm and a T recognition arm, and the targeted sequence comprises, in order from 5' to 3', a first target region, a bulge region, and a second target region,
wherein the A recognition arm is complementary to the first target region, the T recognition arm is complementary to the second target region, and the T recognition arm is located 5' of and adjacent to the A recognition arm in the Short External Guide Sequence, and
wherein the Short External Guide Sequence promotes eukaryotic RNAse P-mediated cleavage of the target RNA molecule.

2. The Short External Guide Sequence of claim 1 wherein the A recognition arm is from 7 to 9 nucleotides long, the T recognition arm is from 5 to 7 nucleotides long, and the bulge region is from 1 to 30 nucleotides long.

3. The Short External Guide Sequence of claim 2 wherein the A recognition arm is 7 or 8 nucleotides long, the T recognition arm is 5 or 6 nucleotides long, and the bulge region is from 5 to 15 nucleotides long.

4. The Short External Guide Sequence of claim 1 wherein the targeted sequence further comprises a turn region wherein the turn region has a sequence of NUNR, where N is any nucleotide, R is any purine nucleotide, and U is a uridine nucleotide.

5. The Short External Guide Sequence of claim 1 wherein the turn region has a sequence of NUCR or UUNR.

6. The Short External Guide Sequence of claim 5 wherein the turn region has a sequence of UUCR.

7. The Short External Guide Sequence of claim 1 comprising a nucleotide base sequence selected from the group consisting of SEQ ID NO. 3, SEQ ID NO. 6, SEQ ID NO: 8, SEQ ID NO: 10, SEQ ID NO: 12, and SEQ ID NO: 14.

8. The Short External Guide Sequence of claim 1 wherein the target RNA molecule is a hepatitis B RNA molecule.

9. A composition for promoting cleavage of a target RNA molecule wherein the composition comprises the Short External Guide Sequence of claim 1 in a pharmaceutically acceptable delivery system.

10. The composition of claim 9 wherein the pharmaceutically acceptable delivery system is selected from the group consisting of liposomes, virosomes, microspheres and microcapsules.

11. The Short External Guide Sequence of claim 1 wherein one or more of the 2' hydroxyl groups of ribonucleotides are replaced with a chemical group selected from the group consisting of hydrogen, an O-alkyl group, an amino group, and fluorine.

12. The Short External Guide Sequence of claim 1 wherein one or more of the phosphate linking groups are replaced with a linking group selected from the group consisting of methyl phosphonate and phosphorothioate.

13. The Short External Guide Sequence of claim 1 wherein one or more of the 2' hydroxyl groups of ribonucleotides are replaced with a chemical group selected from the group consisting of hydrogen, an O-alkyl group, an amino group, and fluorine, and wherein one or more of the phosphate linking groups are replaced with a linking group selected from the group consisting of methyl phosphonate and phosphorothioate.

14. The Short External Guide Sequence of claim 13 wherein one or more of the 2' hydroxyl groups of the ribonucleotides are replaced with hydrogen or a methoxy group, and wherein one or more of the phosphate linking groups are replaced with phosphorothioate.

15. The Short External Guide Sequence of claim 1 wherein the 3' hydroxyl of the Short External Guide Sequence is replaced with a chemical group selected from the group consisting of —OPO(O)OCH$_2$CH(OH)—CH$_2$NH$_2$, —OPO(S)OCH$_2$CH(OH)CH$_2$NH$_2$, and -3'-thymine nucleotide.

16. The Short External Guide Sequence of claim 15 wherein the 3' hydroxyl of the Short External Guide Sequence is replaced with -3'-thymine nucleotide.

17. A method for cleaving a target RNA molecule comprising bringing into contact, under conditions that promote RNAse P-mediated cleavage, RNAse P, the target RNA molecule, and a Short External Guide Sequence oligonucleotide molecule comprising a recognition sequence complementary to regions of a targeted sequence in a target RNA molecule, wherein the recognition sequence comprises an A recognition arm and a T recognition arm, and the targeted sequence comprises, in order from 5' to 3', a first target region, a bulge region, and a second target region, wherein the A recognition arm is complementary to the first target region, the T recognition arm is complementary to the second target region, and the T recognition arm is located 5' of and adjacent to the A recognition arm in the Short External Guide Sequence, and wherein the Short External Guide Sequence promotes eukaryotic RNAse P-mediated cleavage of the target RNA molecule.

18. The method of claim 17 wherein the target RNA molecule is a viral RNA molecule, wherein the step of bringing into contact is accomplished by administering to a patient or cells from a patient the Short External Guide Sequence, and wherein the Short External Guide Sequence is in a pharmaceutically acceptable delivery system.

19. The method of claim 18 wherein the pharmaceutically acceptable delivery system is selected from the group consisting of liposomes, virosomes, microspheres and microcapsules.

20. The method of claim 18 wherein the viral RNA molecule is a hepatitis B RNA molecule.

21. A method of inhibiting a virus comprising exposing said virus to a Short External Guide Sequence oligonucleotide, wherein the Short External Guide Sequence oligonucleotide comprises a recognition sequence complimentary to regions of a target sequence in a target RNA molecule, wherein the recognition sequence comprises an A recognition arm and a T recognition arm, and the targeted sequence comprises, in order from 5' to 3', a first target region, a bulge region, and a second target region, wherein the A recognition arm is complementary to the first target region, the T arm is complementary to the second target region, and the T arm is located 5' of and adjacent to the A recognition arm in the Short External Guide Sequence, and wherein the Short External Guide Sequence promotes eukaryotic RNAse P-mediated cleavage of the target RNA molecule.

22. An engineered expression vector encoding a Short External Guide Sequence oligonucleotide molecule comprising a recognition sequence complementary to regions of a targeted sequence in a target RNA molecule, wherein the recognition sequence comprises an A recognition arm and a T recognition arm, and the targeted sequence comprises, in order from 5' to 3', a first target region, a bulge region, and a second target region, wherein the A recognition arm is complementary to the first target region, the T recognition arm is complementary to the second target region, and the T recognition arm is located 5' of and adjacent to the A recognition arm in the Short External Guide Sequence, and wherein the Short External Guide Sequence promotes eukaryotic RNAse P-mediated cleavage of the target RNA molecule.

23. The Short External Guide Sequence of claim 1 further comprising a RNA sequence binding to a ligand wherein the Short External Guide Sequence promotes cleavage of the target RNA molecule by RNAse P only when bound to the ligand.

24. The Short External Guide Sequence of claim 1 further comprising a RNA sequence binding to a ligand wherein the Short External Guide Sequence promotes cleavage of the target RNA molecule by RNAse P only when not bound to the ligand.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:1:

AAUCCUUCCC CCACC     15

( 2 ) INFORMATION FOR SEQ ID NO:2:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:2:

GCACGGAAUU CGGUGGGGCC AGCUCCUGAA GGUUCGAAAA AAA     43

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:3:

AAUCCACUGC ACUAG     15

( 2 ) INFORMATION FOR SEQ ID NO:4:

( i ) SEQUENCE CHARACTERISTICS:
          ( A ) LENGTH: 43 base pairs
          ( B ) TYPE: nucleic acid
          ( C ) STRANDEDNESS: single
          ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:4:

```
GGCUCAGUUU   ACUAGUGCCA   UUUGUUCAGU   GGUUCGAAAA   AAA                    43
```

( 2 ) INFORMATION FOR SEQ ID NO:5:

( i ) SEQUENCE CHARACTERISTICS:
          ( A ) LENGTH: 51 base pairs
          ( B ) TYPE: nucleic acid
          ( C ) STRANDEDNESS: single
          ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:5:

```
GGCUCAGUUU   ACUAGUGCCA   UUUGUUCAGU   GGUUCGAAUC   CACUGCACUA   G          51
```

( 2 ) INFORMATION FOR SEQ ID NO:6:

( i ) SEQUENCE CHARACTERISTICS:
          ( A ) LENGTH: 13 base pairs
          ( B ) TYPE: nucleic acid
          ( C ) STRANDEDNESS: single
          ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:6:

```
GAGGAAACGC   CGC                                                           13
```

( 2 ) INFORMATION FOR SEQ ID NO:7:

( i ) SEQUENCE CHARACTERISTICS:
          ( A ) LENGTH: 50 base pairs
          ( B ) TYPE: nucleic acid
          ( C ) STRANDEDNESS: single
          ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:7:

```
CUGGAUGUGU   CUGCGGCGUU   UUAUCAUCUU   CCUCUUCAUC   CUGCUGCUAU             50
```

( 2 ) INFORMATION FOR SEQ ID NO:8:

( i ) SEQUENCE CHARACTERISTICS:
          ( A ) LENGTH: 13 base pairs ( B ) TYPE: nucleic acid
( C ) STRANDEDNESS: single
( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:8:

GGUUUGGGGA UAC                                                                                   13

( 2 ) INFORMATION FOR SEQ ID NO:9:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:9:

AGGAACCUCU AUGUAUCCCU CCUGUUGCUG UACCAAACCU UCGGACGGAA AUUGCA       56

( 2 ) INFORMATION FOR SEQ ID NO:10:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:10:

CCACUGAUGG CAC                                                                                   13

( 2 ) INFORMATION FOR SEQ ID NO:11:

( i ) SEQUENCE CHARACTERISTICS:
( A ) LENGTH: 46 base pairs
( B ) TYPE: nucleic acid
( C ) STRANDEDNESS: single
( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:11:

CUCAGUUUAC UAGUGCCAUU UGUUCAGUGG UUCGUAGGGC UUUCCC                  46

( 2 ) INFORMATION FOR SEQ ID NO:12:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear (i i) MOLECULE TYPE: RNA (i i i) HYPOTHETICAL: NO (i v) ANTI-SENSE: NO (x i) SEQUENCE DESCRIPTION: SEQ ID NO:12:

GCGAAGGUCC GGC 13

(2) INFORMATION FOR SEQ ID NO:13:

(i) SEQUENCE CHARACTERISTICS:
(A) LENGTH: 48 base pairs
(B) TYPE: nucleic acid
(C) STRANDEDNESS: single
(D) TOPOLOGY: linear (i i) MOLECULE TYPE: RNA (i i i) HYPOTHETICAL: NO (i v) ANTI-SENSE: NO (x i) SEQUENCE DESCRIPTION: SEQ ID NO:13:

GCCUUCUCAU CUGCCGGACC GUGUGCACUU CGCUUCACCU CUGCACGU 48

(2) INFORMATION FOR SEQ ID NO:14:

(i) SEQUENCE CHARACTERISTICS:
(A) LENGTH: 13 base pairs
(B) TYPE: nucleic acid
(C) STRANDEDNESS: single
(D) TOPOLOGY: linear (i i) MOLECULE TYPE: RNA (i i i) HYPOTHETICAL: NO (i v) ANTI-SENSE: NO (x i) SEQUENCE DESCRIPTION: SEQ ID NO:14:

GCGAAGACGG UCC 13

(2) INFORMATION FOR SEQ ID NO:15:

(i) SEQUENCE CHARACTERISTICS:
(A) LENGTH: 51 base pairs
(B) TYPE: nucleic acid
(C) STRANDEDNESS: single
(D) TOPOLOGY: linear (i i) MOLECULE TYPE: RNA (i i i) HYPOTHETICAL: NO (i v) ANTI-SENSE: NO (x i) SEQUENCE DESCRIPTION: SEQ ID NO:15:

GCACGGAAUU CGGUGGGCC AGCUCCUGAA GGUUCGAAUC CUUCCCCAC C 51